US 6,544,561 B2

(12) United States Patent
Beckett

(10) Patent No.: US 6,544,561 B2
(45) Date of Patent: Apr. 8, 2003

(54) AQUEOUS METAL BICARBONATE SOLUTION AND METHOD OF USE

(75) Inventor: Russell John Beckett, Red Hill (AU)

(73) Assignee: The Lachlan Family Pty Ltd. (AU)

( * ) Notice: Subject to any disclaimer, the term of this patent is extended or adjusted under 35 U.S.C. 154(b) by 0 days.

(21) Appl. No.: 09/962,163

(22) Filed: Sep. 26, 2001

(65) Prior Publication Data

US 2002/0064566 A1 May 30, 2002

Related U.S. Application Data

(63) Continuation of application No. 09/422,645, filed on Oct. 22, 1999, now Pat. No. 6,328,997, which is a continuation of application No. 09/041,787, filed on Mar. 13, 1998, now Pat. No. 6,048,553.

(30) Foreign Application Priority Data

Mar. 17, 1997 (AU) ............................... PO5677
Nov. 28, 1997 (AU) ............................... PP0608

(51) Int. Cl.[7] .......................... A61K 33/10; A61K 33/00
(52) U.S. Cl. ....................................... 424/686; 424/717
(58) Field of Search .................................. 424/686, 717

(56) References Cited

U.S. PATENT DOCUMENTS

| 4,489,535 A | 12/1984 | Veltman ....................... 53/431 |
| 4,588,744 A | 5/1986 | McHugh et al. ............. 514/470 |
| 4,663,166 A | 5/1987 | Veech ........................... 424/146 |
| 5,296,242 A | 3/1994 | Zander ......................... 424/717 |
| 5,409,904 A | 4/1995 | Hecht et al. .................... 514/23 |

FOREIGN PATENT DOCUMENTS

| AU | 37798/85 | 8/1985 |
| AU | 29958/92 | 6/1993 |
| AU | 77466/94 | 1/1995 |
| GB | 1453616 | 10/1976 |
| WO | WO89/06133 | 7/1989 |
| WO | WO91/10457 | 7/1991 |
| WO | WO96/00055 | 1/1996 |
| WO | WO96/10409 | 4/1996 |

OTHER PUBLICATIONS

Bouissou, P., et al., Chemical Abstracts, 106:136079 (1986).
Bruton, J. D., et al., Journal of Physiology 459, 445P (1993).

*Primary Examiner*—William R. A. Jarvis
(74) *Attorney, Agent, or Firm*—Jones, Tullar & Cooper, P.C.

(57) ABSTRACT

An aqueous neutral to mildly alkaline metal bicarbonate solution is disclosed. The solution comprises metal bicarbonate dissolved in the solution, the metal bicarbonate comprising bicarbonate anions and metal cations. In addition there is a pH adjusting agent in the solution in an amount whereby the solution is at a neutral to mildly alkaline pH. Also disclosed is a process of preparing an aqueous neutral to mildly alkaline metal bicarbonate solution comprising bicarbonate anions and metal cations. The process comprises reacting a compound selected from the group consisting of metal carbonate, metal carbonate hydroxide, metal oxide, metal hydroxide and any mixture thereof with an effective concentration of a pH adjusting agent to produce the aqueous neutral to mildly alkaline metal bicarbonate solution, wherein the pH adjusting agent is present in an amount whereby the solution is at a neutral to mildly alkaline pH. Further disclosed are a method of preventing and/or treating certain inflammatory diseases and/or degenerative diseases in a mammal, a method of preventing and/or treating certain viral diseases in a mammal, a method of decreasing and/or treating senescence and/or of increasing longevity in a mammal, a method of scavenging protons in a mammal, a method of decreasing proton concentrations in a mammal by altering carbonic anhydrase enzyme reactions in said mammal, a method of decreasing inflammation and/or inflammatory conditions in a mammal and a method of increasing motor activity and/or decreasing fatigue in a mammal.

21 Claims, 3 Drawing Sheets

AQUEOUS METAL BICARBONATE SOLUTION AND METHOD OF USE

CROSS-REFERENCE TO RELATED APPLICATIONS

This is a continuation of Application No. 09/422,645 filed on Oct. 22, 1999, now U.S. Pat. No. 6,328,997, which is a continuation of Application No. 09/041,787 filed on Mar. 13, 1998, now U.S. Pat. No. 6,048,553.

TECHNICAL FIELD

This invention relates to an aqueous metal bicarbonate solution, a process of preparing the aqueous metal bicarbonate solution and a method of preventing and treating certain inflammatory diseases, degenerative diseases and viral diseases in mammals.

Generally the certain inflammatory diseases, degenerative diseases and viral diseases in mammals are those that require extracellular or intracellular acidic conditions or extracellular or intracellular proton concentrations at some point in disease process or disease pathogenesis.

Typically the certain inflammatory diseases, degenerative diseases and viral diseases in mammals are those that require the activities of carbonic anhydrase enzymes and/or the activities of acid (aspartic) protease enzymes and/or the activities of endosomal or lysosomal acid-requiring-enzymes and/or the activities of V-type ATPase proton pumps at some point in disease process or disease pathogenesis. Typically the certain inflammatory diseases, degenerative diseases and viral diseases in mammals are represented by the diseases of arthritis and influenza.

This invention relates to a method of using an aqueous metal bicarbonate solution to decrease senescence and to increase longevity in mammals. Generally senescence is decreased and longevity is increased in mammals by improving the buffering capacity of the extracellular and intracellular fluids of the body. Generally senescence is decreased and longevity is increased in mammals by the improved buffering capacity causing a decrease in proton concentrations in the extracellular and intracellular fluids of the body. Typically senescence is decreased and longevity is increased in mammals by improving the buffering capacity of the extracellular and intracellular bicarbonate buffers. Typically senescence is decreased and longevity is increased in mammals by the improved extracellular and intracellular bicarbonate buffers causing a decrease in proton concentrations.

BACKGROUND ART

Certain inflammatory diseases, degenerative diseases and viral diseases are major causes of morbidity and mortality in mammals. Typically these diseases are represented by the diseases of arthritis and influenza.

Arthritis is any inflammatory condition of the joints, characterised by pain and swelling. Osteoarthritis is the most common form of arthritis in which one or many joints undergo degenerative changes. Treatment includes rest of the involved joints, heat, and antiinflammatory drugs. Intraarticular injections of corticosteroids may give relief. Surgical treatment is sometimes necessary and may reduce pain and greatly improve the function of the joint. However these treatments, apart from surgical treatment, only provide temporary relief and some may have severe side reactions.

Influenza is a highly contagious infection of the respiratory tract caused by a myxovirus and transmitted by airborne droplet infection. It occurs in isolated cases, epidemics and pandemics. Treatment is symptomatic and usually involves bed rest, antipyretics such as aspirin and drinking of fluids. New strains of the virus emerge at regular intervals so it is difficult to take preventative measures to avoid the infection. There is a need for a method to prevent and to treat certain inflammatory diseases, degenerative diseases and viral diseases in mammals. There is a need for a method to prevent and to treat arthritis and influenza in mammals.

Senescence in mammals is characterised by progressive oxidations of the structural and functional molecules that constitute body cells and tissues. Oxidations of the structural and functional molecules in body cells and tissues are increased in rate by acidic conditions. Oxidations of structural and functional molecules are increased in rate by the presence of excess proton concentrations. There is a need for a method to prevent and treat excess proton concentrations in body cells so that oxidations of structural and functional molecules are decreased in rate. There is a need for a method to decrease and treat senescence in mammals.

OBJECTS OF INVENTION

It is an object of this invention to provide an aqueous metal bicarbonate solution to prevent and to treat certain inflammatory diseases, degenerative diseases and viral diseases in mammals. It is a further object of this invention to provide a process of preparing the aqueous metal bicarbonate solution. It is also an object of this invention to provide methods for the prevention and treatment of certain inflammatory diseases, degenerative diseases and viral diseases in mammals using the aqueous metal bicarbonate solution. Generally the certain inflammatory diseases, degenerative diseases and viral diseases in. mammals are those that require extracellular or intracellular acidic conditions or extracellular or intracellular proton concentrations at some point in disease process or disease pathogenesis. Typically the certain inflammatory diseases, degenerative diseases and viral diseases in mammals are those that require the activities of carbonic anhydrase enzymes and/or the activities of acid (aspartic) protease enzymes and/or the activities of endosomal or lysosomal acid-requiring-enzymes and/or the activities of V-type ATPase proton pumps at some point in disease process or disease pathogenesis. Typically the certain inflammatory diseases, degenerative diseases and viral diseases in mammals are represented by the diseases of arthritis and influenza.

It is an object of this invention to provide an aqueous metal bicarbonate solution to decrease senescence and to treat senescence and to increase longevity in mammals. It is a further object of this invention to provide a process of preparing the aqueous metal bicarbonate solution. It is also an object of this invention to provide methods for the decrease of senescence and the treatment of senescence and the increase in longevity in mammals using the aqueous metal bicarbonate solution. Generally senescence is decreased and longevity is increased in mammals by improving the buffering capacity of the extracellular and intracellular fluids of the body. Generally senescence is decreased and longevity is increased in mammals by the improved buffering capacity causing a decrease in proton concentrations in the extracellular and intracellular fluids of the body. Typically senescence is decreased and longevity is increased in mammals by improving the buffering capacity of the extracellular and intracellular bicarbonate buffers. Typically senescence is decreased and longevity is increased in mammals by the improved extracellular and intracellular bicarbonate buffers causing a decrease in proton concentrations.

DISCLOSURE OF INVENTION

According to a first embodiment of the present invention there is provided an aqueous metal bicarbonate solution comprising a stoichiometric concentration of bicarbonate anions and a corresponding substantially stoichiometric concentration of metal cations in association with the bicarbonate anions, the metal bicarbonate being present in a therapeutically effective amount and an acceptable carbon dioxide-containing-aqueous diluent to maintain the metal bicarbonate in the aqueous diluent.

Typically the solution is acceptable for oral administration.

In one embodiment there is provided a combination comprising the solution of the first embodiment in combination with a stabilising agent in an amount effective to maintain and stabilise the bicarbonate anions in the neutral to mildly alkaline solution. Generally the combination is kept in a sealed or closed container at 0.8 to 5 atmospheres, more typically 1 atmosphere at 0–25° C., more typically 0.1–10° C. In one particular embodiment the stabilising agent may be present in the solution in an amount effective to maintain and stabilise the bicarbonate anions in the neutral to mildly alkaline solution. In another particular embodiment the stabilising agent may consist of or comprise a gas above the solution in an amount effective to maintain and stabilise the bicarbonate anions in the neutral to mildly alkaline solution. In a further particular embodiment the stabilising agent may be present in the solution and also may consist of or comprise a gas above the solution, the total amount of stabilising agent in the solution and in the gas above the solution being in an amount effective to maintain and stabilise the bicarbonate anions in the neutral to mildly alkaline solution. The stabilising agent which consists of a gas above the solution may be carbon dioxide. The stabilising agent which comprises a gas above the solution may be carbon dioxide in an an inert gas such as nitrogen, air, oxygen, argon and/or helium, for example. The stabilising agent in the solution may be carbon dioxide dissolved in the solution, hydrated carbon dioxide, carbonic acid, and/or other suitable source of carbon dioxide.

According to a second embodiment of the present invention there is provided a process of preparing an aqueous metal bicarbonate solution comprising a stoichiometric concentration of bicarbonate anions and a corresponding substantially stoichiometric concentration of metal cations in association with the bicarbonate anions, which process comprises reacting a concentration of a metal carbonate or metal carbonate hydroxide or metal oxide or metal hydroxide with a concentration of carbonic acid or hydrated carbon dioxide to produce the metal bicarbonate aqueous solution, wherein said metal bicarbonate being present in a therapeutically effective amount.

Typically the aqueous metal bicarbonate solution has a neutral to mildly alkaline pH. Typically the pH is in the range 7 to 9. Typically the temperature of the aqueous metal bicarbonate solution is maintained at a level to maintain the metal bicarbonate in the aqueous diluent.

According to a third embodiment of the present invention there is provided an aqueous metal bicarbonate solution whenever prepared by the process of the second embodiment.

According to a fourth embodiment of the present invention there is provided a method of preventing and treating certain inflammatory diseases and degenerative diseases in a mammal in need of such prevention or treatment comprising administering to said mammal an effective amount of an aqueous metal bicarbonate solution of the first or third embodiment or a metal bicarbonate.

Generally the certain inflammatory diseases and degenerative diseases in a mammal are those that require extracellular or intracellular acidic conditions or extracellular or intracellular proton concentrations at some point in disease process or disease pathogenesis.

Typically the certain inflammatory diseases and degenerative diseases in a mammal are those that require the activities of carbonic anhydrase enzymes and/or the activities of acid (aspartic) protease enzymes and/or the activities of endosomal or lysosomal acid-requiring-enzymes and/or the activities of V-type ATPase proton pumps at some point in disease process or disease pathogenesis.

Typically the certain inflammatory diseases or degenerative diseases may present as arthritis. Typically the arthritis may present as osteoarthritis.

According to a fifth embodiment of the present invention there is provided a method of preventing and treating certain viral diseases in a mammal in need of such prevention or treatment comprising administering to said mammal an effective amount of an aqueous metal bicarbonate solution of the first or third embodiment or a metal bicarbonate.

Typically the certain viral diseases require intracellular acidic conditions or intracellular proton concentrations for either removal of viral protein coats or assembly of viral protein coats. Typically the viral diseases may present as influenza.

According to a sixth embodiment of the present invention there is provided a method of decreasing and treating senescence and of increasing longevity in a mammal comprising administering to said mammal an effective amount of an aqueous metal bicarbonate solution of the first or third embodiment or a metal bicarbonate.

Typically senescence is decreased and longevity is increased by maintaining or increasing normal extracellular and/or intracellular alkaline conditions. Typically senescence is decreased and longevity is increased by improving the buffering capacity of the extracellular and intracellular fluids of the body. Typically longevity is increased by maintaining or increasing normal mitochondrial alkaline conditions. Typically longevity is increased by decreasing extracellular and intracellular acidic conditions or by decreasing extracellular and intracellular proton concentrations.

Typically senescence is decreased and longevity is increased in mammals by improving the buffering capacity of the extracellular and intracellular bicarbonate buffers. Typically senescence is decreased and longevity is increased in mammals by the improved extracellular and intracellular bicarbonate buffers causing a decrease in proton concentrations. Typically senescence is decreased and longevity is increased by preventing or treating certain inflammatory diseases, degenerative diseases and viral diseases in mammals. Typically longevity is increased by decreasing the morbidity and mortality associated with these diseases.

According to a seventh embodiment of the present invention there is provided a method of scavenging protons in a mammal comprising administering to said mammal an effective amount of a proton scavenger.

Typically the proton scavenger comprises a metal bicarbonate. Typically the metal bicarbonate is in the form of the aqueous metal bicarbonate solution of the first or third embodiment.

According to an eighth embodiment of the present invention there is provided a method of decreasing proton concentrations in a mammal by altering carbonic anhydrase enzyme reactions in said mammal comprising administering to said mammal an effective amount of an aqueous metal bicarbonate solution of the first or third embodiment or a metal bicarbonate.

According to a ninth embodiment of the present invention there is provided a method of decreasing inflammation and inflammatory conditions in a mammal comprising administering to said mammal an effective amount of an aqueous metal bicarbonate solution of the first or third embodiment or a metal bicarbonate.

Generally inflammation and inflammatory conditions are decreased by decreasing the extracellular and intracellular acidic conditions that are required for inflammatory processes. Generally inflammation and inflammatory conditions are decreased by decreasing the extracellular and intracellular proton concentrations that are required for inflammatory processes. Typically inflammation is decreased by altering carbonic anhydrase enzyme reactions and/or decreasing the activities of acid (aspartic) protease enzymes and/or decreasing the activities of endosomal or lysosomal acid-requiring-enzymes and/or decreasing the activities of V-type ATPase proton pumps.

According to a tenth embodiment of the present invention there is provided a method of increasing motor activity in a mammal comprising administering to said mammal an effective amount of an aqueous metal bicarbonate solution of the first or third embodiment or a metal bicarbonate.

Typically motor activity is increased by decreasing extracellular and intracellular acidic conditions or by decreasing extracellular and intracellular proton concentrations. Typically motor activity is increased by improving the buffering capacity of extracellular and intracellular fluids. Typically motor activity is increased by improving the buffering capacity of the extracellular and intracellular bicarbonate buffers. Typically motor activity is increased by increasing extracellular and intracellular alkaline conditions. Typically motor activity is increased by scavenging protons produced by ATP hydrolysis, lactic acid production, lipid metabolism and other metabolic processes.

According to an eleventh embodiment of the present invention there is provided an aqueous neutral to mildly alkaline metal bicarbonate solution, comprising metal bicarbonate dissolved in the solution, said metal bicarbonate comprising bicarbonate anions and metal cations, and a pH adjusting agent in the solution in an amount whereby the solution is at a neutral to mildly alkaline pH.

Typically a corresponding substantially stoichiometric concentration of metal cations are in association with the bicarbonate anions. Typically the solution is acceptable for oral administration.

In one embodiment there is provided a combination comprising a substantially stable aqueous neutral to mildly alkaline metal bicarbonate solution, comprising metal bicarbonate dissolved in the solution, said metal bicarbonate comprising bicarbonate anions and metal cations, and a pH adjusting agent in the solution in an amount whereby the solution is at a neutral to mildly alkaline pH, in combination with a stabilising agent in an amount effective to maintain and stabilise the bicarbonate anions in the neutral to mildly alkaline solution. In another embodiment there is provided a combination comprising a substantially stable aqueous neutral to mildly alkaline metal bicarbonate solution, comprising metal bicarbonate dissolved in the solution, said metal bicarbonate comprising bicarbonate anions and metal cations, in combination with a stabilising agent in an amount effective to maintain and stabilise the bicarbonate anions in the solution whereby the solution is at a neutral to mildly alkaline pH.

The pH adjusting agent and the stabilising agent may be the same or different. Generally the combination is kept in a sealed or closed container at 0.8 to 5 atmospheres, more typically 1 atmosphere at 0–25° C., more typically 0.1–10° C.

In one particular embodiment the stabilising agent may be present in the solution in an amount effective to maintain and stabilise the bicarbonate anions in the neutral to mildly alkaline solution. In another particular embodiment the stabilising agent may consist of or comprise a gas above the solution in an amount effective to maintain and stabilise the bicarbonate anions in the neutral to mildly alkaline solution. In a further particular embodiment the stabilising agent may be present in the solution and may consist of or comprise a gas above the solution, the total amount of stabilising agent in the solution and in the gas above the solution being in an amount effective to maintain and stabilise the bicarbonate anions in the neutral to mildly alkaline solution. The stabilising agent which consists of a gas above the solution may be carbon dioxide. The stabilising agent which comprises a gas above the solution may be carbon dioxide in an an inert gas such as nitrogen, air, oxygen, argon and/or helium, for example. The stabilising agent in the solution may be carbon dioxide dissolved in the solution, hydrated carbon dioxide, carbonic acid, and/or other suitable source of carbon dioxide.

According to a twelfth embodiment of the present invention there is provided a solution for preventing and/or treating certain inflammatory diseases and/or degenerative diseases and/or certain viral diseases in a mammal, comprising the aqueous neutral to mildly alkaline metal bicarbonate solution of the eleventh embodiment whereby the metal bicarbonate is present in an amount effective to prevent and/or treat said diseases.

According to a thirteenth embodiment of the present invention there is provided a solution for decreasing and/or treating senescence and/or increasing longevity in a mammal, comprising the aqueous neutral to mildly alkaline metal bicarbonate solution of the eleventh embodiment whereby the metal bicarbonate is present in an amount effective to decrease and/or treat senescence and/or increase longevity.

According to a fourteenth embodiment of the present invention there is provided a solution for scavenging protons in a mammal, comprising the aqueous neutral to mildly alkaline metal bicarbonate solution of the eleventh embodiment whereby the metal bicarbonate is present in an amount effective to scavenge protons.

According to a fifteenth embodiment of the present invention there is provided a solution for decreasing proton concentrations in a mammal, comprising the aqueous neutral to mildly alkaline metal bicarbonate solution of the eleventh embodiment whereby the metal bicarbonate is present in an amount effective to decrease proton concentrations.

According to a sixteenth embodiment of the present invention there is provided a solution for decreasing inflammation and inflammatory conditions in a mammal, comprising the aqueous neutral to mildly alkaline metal bicarbonate solution of the eleventh embodiment whereby the metal bicarbonate is present in an amount effective to decrease inflammation and/or inflammatory conditions.

According to a seventeenth embodiment of the present invention there is provided a solution for increasing motor activity and/or decrease fatigue in a mammal, comprising the aqueous neutral to mildly alkaline metal bicarbonate solution of the eleventh embodiment whereby the metal bicarbonate is present in an amount effective to increase motor activity.

According to an eighteenth embodiment of the present invention there is provided a process of preparing an aqueous neutral to mildly alkaline metal bicarbonate solution comprising bicarbonate anions and metal cations, which process comprises reacting a compound selected from the group consisting of metal carbonate, metal carbonate hydroxide, metal oxide, metal hydroxide and any mixture thereof with an effective concentration of a pH adjusting agent to produce the aqueous neutral to mildly alkaline metal bicarbonate solution, wherein the pH adjusting agent is present in an amount whereby the solution is at a neutral to mildly alkaline pH.

Typically a corresponding substantially stoichiometric concentration of metal cations are in association with the bicarbonate anions. Generally the solution is stored in a sealed or closed container at 0.8 to 5 atmospheres, more typically 1 atmosphere at 0–25° C., more typically 0.1–10° C. In one embodiment the process further comprises combining the solution with a stabilising agent in an amount effective to maintain and stabilise the bicarbonate anions in the neutral to mildly alkaline solution. In one particular embodiment the process comprises conducting the process under gaseous atmosphere comprising a stabilising agent in an amount effective to maintain and stabilise the bicarbonate anions in the neutral to mildly alkaline solution. The stabilising agent may be carbon dioxide or comprise carbon dioxide in an inert gas such as nitrogen, air, oxygen, argon and/or helium, for example. Generally the combination is stored in a sealed or closed container at 0.8 to 5 atmospheres, more typically 1 atmosphere at 0–25° C., more typically 0.1–10° C.

One particular embodiment may comprise adding the stabilising agent to the solution in the solution in an amount effective to maintain and stabilise the bicarbonate anions in the neutral to mildly alkaline solution. Another particular embodiment may comprise blanketing the solution with a gas consisting of or comprising the stabilising agent in an amount effective to maintain and stabilise the bicarbonate anions in the neutral to mildly alkaline solution. A further particular embodiment may comprise adding the stabilising agent to the solution in the solution and blanketing the solution with a gas consisting of or comprising the stabilising agent, the total amount of stabilising agent in the solution and in the gas above the solution being in an amount effective to maintain and stabilise the bicarbonate anions in the neutral to mildly alkaline solution. The stabilising agent which consists of a gas above the solution may be carbon dioxide. The stabilising agent which comprises a gas above the solution may be carbon dioxide in an inert gas such as nitrogen, air, oxygen, argon and/or helium, for example. The stabilising agent in the solution may be carbon dioxide dissolved in the solution, hydrated carbon dioxide, carbonic acid, and/or other suitable source of carbon dioxide.

According to a nineteenth embodiment of the present invention there is provided a aqueous neutral to mildly alkaline metal bicarbonate solution whenever prepared by the process of the eighteenth embodiment.

According to a twentieth embodiment of the present invention there is provided a method of preventing and/or treating certain inflammatory diseases and/or degenerative diseases in a mammal in need of such prevention and/or treatment comprising administering to said mammal an effective amount of an aqueous neutral to mildly alkaline metal bicarbonate solution of the eleventh or a metal bicarbonate.

Generally the certain inflammatory diseases and degenerative diseases in a mammal are those that require extracellular or intracellular acidic conditions or extracellular or intracellular proton concentrations at some point in disease process or disease pathogenesis.

Typically the certain inflammatory diseases and degenerative diseases in a mammal are those that require the activities of carbonic anhydrase enzymes and/or the activities of acid (aspartic) protease enzymes and/or the activities of endosomal or lysosomal acid-requiring-enzymes and/or the activities of V-type ATPase proton pumps at some point in disease process or disease pathogenesis.

Typically the certain inflammatory diseases or degenerative diseases may present as arthritis. Typically the arthritis may present as osteoarthritis.

According to a twenty-first embodiment of the present invention there is provided a method of preventing and/or treating certain viral diseases in a mammal in need of such prevention and/or treatment comprising administering to said mammal an effective amount of an aqueous neutral to mildly alkaline metal bicarbonate solution of the eleventh embodiment or a metal bicarbonate.

Typically the certain viral diseases require intracellular acidic conditions or intracellular proton concentrations for either removal of viral protein coats or assembly of viral protein coats. Typically the viral diseases may present as influenza.

According to a twenty-second embodiment of the present invention there is provided a method of decreasing and/or treating senescence and/or of increasing longevity in a mammal comprising administering to said mammal an effective amount of an aqueous neutral to mildly alkaline metal bicarbonate solution of the eleventh embodiment or a metal bicarbonate.

Typically senescence is decreased and longevity is increased by maintaining or increasing normal extracellular and/or intracellular alkaline conditions. Typically senescence is decreased and longevity is increased by improving the buffering capacity of the extracellular and intracellular fluids of the body. Typically longevity is increased by maintaining or increasing normal mitochondrial alkaline conditions. Typically longevity is increased by decreasing extracellular and intracellular acidic conditions or by decreasing extracellular and intracellular proton concentrations. Typically senescence is decreased and longevity is increased in mammals by improving the buffering capacity of the extracellular and intracellular bicarbonate buffers. Typically senescence is decreased and longevity is increased in mammals by the improved extracellular and intracellular bicarbonate buffers causing a decrease in proton concentrations.

Typically senescence is decreased and longevity is increased by preventing or treating certain inflammatory diseases, degenerative diseases and viral diseases in mammals. Typically longevity is increased by decreasing the morbidity and mortality associated with these diseases.

According to a twenty-third embodiment of the present invention there is provided a method of scavenging protons in a mammal comprising administering to said mammal an effective amount of a proton scavenger.

Typically the proton scavenger comprises a metal bicarbonate. Typically the metal bicarbonate is in the form of the aqueous neutral to mildly alkaline metal bicarbonate solution of the eleventh embodiment.

According to a twenty-fourth embodiment of the present invention there is provided a method of decreasing proton concentrations in a mammal by altering carbonic anhydrase enzyme reactions in said mammal comprising administering to said mammal an effective amount of an aqueous neutral to mildly alkaline metal bicarbonate solution of the eleventh embodiment or a metal bicarbonate.

According to a twenty-fifth embodiment of the present invention there is provided a method of decreasing inflammation and/or inflammatory conditions in a mammal comprising administering to said mammal an effective amount of an aqueous neutral to mildly alkaline metal bicarbonate solution of the eleventh embodiment or a metal bicarbonate.

Generally inflammation and inflammatory conditions are decreased by decreasing the extracellular and intracellular acidic conditions that are required for inflammatory processes. Generally inflammation and inflammatory conditions are decreased by decreasing the extracellular and intracellular proton concentrations that are required for inflammatory processes. Typically inflammation is decreased by altering carbonic anhydrase enzyme reactions and/or decreasing the activities of acid (aspartic) protease enzymes and/or decreasing the activities of endosomal or lysosoinal acid-requiring-enzymes and/or decreasing the activities of V-type ATPase proton pumps.

According to a twenty-sixth embodiment of the present invention there is provided a method of increasing motor activity and/or decreasing fatigue in a mammal comprising administering to said mammal an effective amount of an aqueous neutral to mildly alkaline metal bicarbonate solution of the eleventh embodiment or a metal bicarbonate.

The methods of the invention typically involve orally administering to the mammal, the mammal being typically human. Further the methods of the invention typically involve orally administering to a mammal in need of treatment for the specified condition of the particular embodiment, the mammal being typically human. Typically motor activity is increased by decreasing extracellular and intracellular acidic conditions or by decreasing extracellular and intracellular proton concentrations. Typically motor activity is increased by improving the buffering capacity of extracellular and intracellular fluids. Typically motor activity is increased by improving the buffering capacity of the extracellular and intracellular bicarbonate buffers. Typically motor activity is increased by increasing extracellular and intracellular alkaline conditions. Typically motor activity is increased by scavenging protons produced by ATP hydrolysis, lactic acid production, lipid metabolism and other metabolic processes.

The term mammal as used herein includes vertebrate. Examples of mammals and vertebrates to which the methods of the invention apply include a bovine, human (male or female), ovine, equine, caprine, Leporine, feline or canine mammal or vertebrate. Specific examples of animals include sheep, cattle, horses, rabbits, cats, goats, alpacas, cats, dogs, pigs, rabbits, fowls, deer, buffaloes and other livestock and domestic animals.

Metal Bicarbonate Generally

Generally the pH of the aqueous metal bicarbonate solution is neutral to mildly alkaline, typically mildly alkaline and more typically in the range of 7 to 9 even more typically 8 to 8.6 and the temperature of the aqueous neutral to mildly alkaline metal bicarbonate solution is maintained at such a level so as to maintain the metal bicarbonate in the aqueous diluent. The aqueous neutral to mildly alkaline metal bicarbonate solution may be kept under an atmosphere comprising carbon dioxide of from about 0.8 to 5 or 1 to 5 atmospheres, more typically 1 to 3 atmospheres and even more typically slightly above atmospheric pressure such as the sorts of pressures that soft drinks are currently under in cans or bottles, for example, so as to maintain the metal bicarbonate in the aqueous diluent.

Generally the metal cation is an alkaline earth metal cation or an alkali metal cation. Generally a metal cation is chosen which is capable of acting as a bicarbonate transporter into mammalian cells. More particularly the metal cation may be cations of magnesium, sodium, potassium, calcium, lithium or any mixture thereof. Where a mixture of alkaline earth metal cations or alkali metal cations are used: (1) two different alkaline earth metal cations or alkali metal cations or mixtures thereof, the molar ratio of the first metal cation to the second may be in the range 0.5:99.5 to 99.5:0.5, typically 75:25 to 25:75, more typically 0.7:1 to 1:0.7; (2) three different alkaline earth metal cations or alkali metal cations or mixtures thereof, the molar ratio of the first metal cation to the second to the third may be in the range 99.5:0.5:0.5 to 0.5:99.5:99.5, typically 75:25:25 to 25:75:75, more typically 0.5:1:1 to 1:0.5:0.5; (3) four different alkaline earth metal cations or alkali metal cations or mixtures thereof, the molar ratio of the first metal cation to the second to the third to the fourth may be in the range 99.5:0.5:0.5:0.5 to 0.5:99.5:99.5:99.5, typically 75:25:25:25 to 25:75:75:75, more typically 0.5:1:1:1 to 0.5:1:1:1. Generally the metal cation is magnesium or a mixture of magnesium and sodium metal cations. Typically the aqueous neutral to mildly alkaline metal bicarbonate solution has a high metal cation concentration in association with bicarbonate anions.

Typically the metal bicarbonate is used at a concentration of 10–100 mole% or weight% of its saturation solubility (which will depend on the actual metal bicarbonate(s) used), more typically 10–90%, 10–80%, 10–70%, 10–60%, 10–50%, 10–40%, 10–30%, 10–20%, more typically 15–95%, 15–85%, 15–75%, 15–65%, 15–55%, 15–45%, 15–35%, 15–25%, more typically 15–90%, 15–80%, 15–70%, 15–60%, 15–50%, 15–40%, 15–30%, 15–20%, more typically 10–95%, 10–85%, 10–75%, 10–65%, 10–55%, 10–45%, 10–35%, 10–25%, more typically 20–90%, 20–80%, 20–70%, 20–60%, 20–50%, 20–40%, 20–30%, more typically 25–95%, 25–85%, 25–75%, 25–65%, 25–55%, 25–45%, 25–35%, more typically 25–90%, 25–80%, 25–70%, 25–60%, 25–50%, 25–40%, 25–30%, more typically 20–95%, 20–85%, 20–75%, 20–65%, 20–55%, 2045%, 20–35%, more typically 30–90%, 30–80%, 30–70%, 30–60%, 30–50%, 3040%, more typically 35–95%, 35–85%, 35–75%, 35–65%, 35–55%, 35–45%, more typically 35–90%, 35–80%, 35–70%, 35–60%, 35–50%, 35–40%, more typically 30–95%, 30–85%, 30–75 %, 30–65%, 30–55%, 3045%, more typically 40–90%, 40–80%, 40–70%, 40–60%, 40–50%, more typically 45–95%, 45–85%, 45–75%, 45–65 %, 45–55%, more typically 45–90%, 45–80%, 45–70%, 45–60%, 45–50%, more typically 40–95%, 40–85%, 40–75 %, 40–65%, 40–55%, more typically 50–90%, 50–80%, 50–70%, 50–60%, more typically 55–95%, 55–85%, 55–75%, 55–65%, more typically 55–90%, 55–80%, 55–70%, 55–60%, more typically 50–95%, 50–85%, 50–75%, 50–65%, more typically 60–90%, 60–80%, 60–70%, more typically 65–95%, 65–85%, 65–75%, more typically 65–90%, 65–80%, 65–70%, more typically 60–95%, 60–85%, 60–75%, more typically 70–90%, 70–80%, more typically 75–95%, 75–85%, more typically 75–90%, 75–80%, more typically 70–95%, 70–85%, more typically 80–90%, more typically 85–95%, more typically 85–90%, more typically 80–95%, more typically 20–100%, 30–100%, 40–100%, 50–100%, 60–100%, 70–100%, 80–100% or 90–100%. Depending on the solubility of the metal bicarbonate, the amount of metal cation may range from 20 mg to 1250 mg or 25 mg to 1250 mg per liter of aqueous neutral to mildly alkaline metal bicarbonate solution, typically 20 mg to 1000 mg or 50 mg to 1000 mg per liter of aqueous neutral to mildly alkaline metal bicarbonate solution, more typically 20mg to 750mg or 50 mg to 750 mg or 20 mg to 600 mg or 50 mg to 600 mg per liter of aqueous neutral to mildly alkaline metal bicarbonate solution, even more typically 20 mg to 500 mg or 30 mg to 500 mg or 50 mg to 500 mg per liter of aqueous neutral to mildly alkaline metal bicarbonate solution, even more typically 20 mg to 250 mg or 50 mg to 250 mg per liter of aqueous neutral to mildly alkaline metal bicarbonate solution, most typically 100 mg to 500 mg or 100 mg to 400 mg or 100 mg to 300 mg or 100 mg to 250 mg per liter of aqueous neutral to mildly alkaline metal bicarbonate solution, even most typically 20 mg to 200 mg or 20 to 150 mg or 20 mg to 120 mg or 120 mg to 300 mg or 120 mg to 200 mg. Typically when the metal cation is magnesium, the amount of magnesium may range from 30 mg to 140 mg per liter of aqueous neutral to mildly alkaline metal bicarbonate solution, typically 30 mg to 130 mg, 30 mg to 120 mg, 30 mg to 110 mg, 30 mg to 100 mg, 30 mg to 90 mg, 30 mg to 80 mg, 30 mg to 70 mg, 30 mg to 60 mg, 30 mg to 50 mg, 30 mg to 40 mg, 50 mg to 120 mg, 60 mg to 120 mg, 70 mg to 120 mg, 80 mg to 120 mg, 90 mg to 120 mg or 75 mg to 120 mg or 100 mg to 120 mg per liter of aqueous neutral to mildly alkaline metal bicarbonate solution. Typically when the metal cation is sodium and/or potassium, the amount of sodium and/or potassium may range from greater than 30 mg to 1250 mg per liter of aqueous neutral to mildly alkaline metal bicarbonate solution, typically 50 mg to 1000 mg or 50 mg to 750 mg or 50 mg to 500 mg or 75 mg to 1250 mg or 75 mg to 1000 mg or 75 mg to 500 mg or 100 mg to 1000 mg or 100 mg to 500 mg or 250 mg to 1000 mg or 250 mg to 500 mg per liter of aqueous neutral to mildly alkaline metal bicarbonate solution. Typically when the metal cation is calcium, the amount of calcium may range from greater than 20mg to 1250 mg per liter of aqueous neutral to mildly alkaline metal bicarbonate solution, typically 20 mg to 1000 mg or 20 mg to 750 mg or 20 mg to 500 mg or 20 mg to 250 mg or 20 mg to 200 mg or 20 mg to 150 mg or 20 mg to 100 mg per liter of aqueous neutral to mildly alkaline metal bicarbonate solution. Typically the amount of bicarbonate anion present will be stoichiometric with the amount of metal cation in solution so as to form the metal bicarbonate. Alternatively, the concentration of the metal bicarbonate can be based on the bicarbonate anion concentrations in which case the amount of bicarbonate anion (which will depend on the saturation solubility of the actual metal bicarbonate anion(s) used). The concentration of bicarbonate typically ranges from 120 mg or 150 mg to 3500 mg per liter of aqueous neutral to mildly alkaline metal bicarbonate solution, typically 120 mg or 150 mg to 3000 mg or 200 mg to 3000 mg per liter of aqueous neutral to mildly alkaline metal bicarbonate solution, more typically 250 mg to 2100 mg or 300 mg to 2000 mg or 200 mg to 1500 mg or 300 mg to 1500 mg or 400 mg to 1500 mg or 500 mg to 1500 mg or 600 mg to 1500 mg or 700 mg to 1500 mg or 800 mg to 1500 mg or 900 mg to 1500 mg or 1000 mg to 1500 mg or 200 mg to 1000 mg or 300 mg to 1000 mg or 400 mg to 1000 mg or 500 mg to 1000 mg or 600 mg to 1000 mg or 700 mg to 1000 mg or 800 mg to 1000 mg or 900 mg to 1000 mg or 1000 mg to 1500 mg or 1200 mg to 1500 mg per liter of aqueous neutral to mildly alkaline metal bicarbonate solution, even more typically 600 mg to 1000 mg or 500 mg to 1500 mg per liter of aqueous neutral to mildly aLkaline metal bicarbonate solution, most typically 950 mg or 200 mg to 2000 mg or 200 mg to 1750 mg or 200 mg to 1250 mg or 200 mg to 100 mg per liter of aqueous neutral to mildly alkaline metal bicarbonate solution. Typically at least 600 mg of bicarbonate anions per liter of solution is present, more typically 600–1800 mg/l, 600–1500 mg/l, 600–1350 mg/l, 600–1200 mg,/l 600–1100 mg/l, 600–1000 mg/l, 600–950 mg/l, 600–900 mg/l, 600–850 mg/l, 600–800 mg/l, 600–750 mg/l, 600–700 mg/l or 600–650 mg/l. Typically a mildly alkaline saturated magnesium bicarbonate solution is used or a mildly alkaline solution comprising a mixture of sodium and/or potassium and magnesium bicarbonate, more typically sodium and magnesium bicarbonate. Typically the range for a mixture of sodium and/or potassium and magnesium bicarbonate, more typically sodium and magnesium bicarbonate varies from 20 mg to 1250 mg or 25 mg to 1250 mg per liter of aqueous neutral to mildly alkaline metal bicarbonate solution, typically 20 mg to 100 mg or 50 mg to 1000 mg per liter of aqueous neutral to mildly alkaline metal bicarbonate solution, more typically 20 mg to 750 mg or 50 mg to 750 mg or 20 mg to 600 mg or 50 mg to 600 mg per liter of aqueous neutral to mildly alkaline metal bicarbonate solution, even more typically 20 mg to 500 mg or 30 mg to 500 mg or 50 mg to 500 mg per liter of aqueous neutral to mildly alkaline metal bicarbonate solution, even more typically 20 mg to 250 mg or 50 mg to 250 mg or even more typically 20 mg to 300 mg or 50 mg to 300 mg per liter of aqueous neutral to mildly alkaline metal bicarbonate solution, most typically 75 mg to 1000 mg or 75 mg to 500 mg or 100 mg to 1000 mg or 100 mg to 500 mg or 100 mg to 400 mg or 100 mg to 300 mg or 100 mg to 250 mg per liter of aqueous neutral to mildly alkaline metal bicarbonate solution, even most typically 20 mg to 200 mg or 20 to 150 mg or 20 mg to 120 mg or 120 mg to 300 mg or 120 mg to 200 mg. Usually the ratio (weight to weight) of magnesium to sodium is in the range 25:1 to 1:4, typically 1:1.125.

Generally the aqueous diluent is water or comprises water. Generally the carbon dioxide-containing-aqueous diluent may be carbonic acid in water, hydrated carbon dioxide in water, carbon dioxide gas dissolved in water, carbonated soft drinks, carbonated mineral water, soda water or other carbon dioxide-containing-aqueous diluents. If carbon dioxide gas is used, the carbon dioxide may be either bubbled into aqueous solutions containing metal carbonate or metal carbonate hydroxide or metal oxide or mixture thereof or the carbon dioxide may be introduced in the form of a blanket over aqueous solutions containing metal carbonate or metal carbonate hydroxide or metal oxide or mixture thereof. Typically the carbon dioxide-containing-aqueous diluent is pharmaceutically acceptable. Typically carbonated mineral water, carbonic acid, hydrated carbon dioxide in water or carbonated water is used. The amounts of carbon dioxide-containing-aqueous diluent and metal carbonate or metal carbonate hydroxide or metal oxide or mixture thereof used are sufficient to obtain a clear solution at a neutral to mildly alkaline pH, typically pH 7 to 9 or pH 7 to 8.6, more typically pH 7.5 to 8.8 or pH 7.5 to 8.5 or pH 7.8 to 8.6, pH 7.8 to 8.5, pH 7.8 to 8.4, pH 7.8 to 8.3, pH 7.8 to 8.2, pH 7.8 to 8.1, pH 7.8 to 8.0, pH 7.8 to 7.9, pH 7.9 to 8.6, pH 7.9 to 8.5, pH 7.9 to 8.4, pH 7.9 to 8.3, pH 7.9 to 8.2, pH 7.9 to 8.1, pH 7.9 to 8.0, pH 8.0 to 8.6, pH 8.0 to 8.5, pH 8.0 to 8.4, pH 8.0 to 8.3, pH 8.0 to 8.2, pH 8.0 to 8.1, pH 8.1 to 8.6, pH 8.1 to 8.5, pH 8.1 to 8.4, pH 8.1 to 8.3, pH 8.1 to 8.2, pH 8.2 to 8.6, pH 8.2 to 8.5, pH 8.2 to 8.4, pH 8.2 to 8.3, pH 8.3 to 8.6, pH 8.3 to 8.5, pH 8.3 to 8.4, pH 8.4 to 8.6, pH 8.4 to 8.5, pH 8.5 to 8.6, even more typically pH 8 to 8.5 or pH 8.2 to 8.6, most typically pH 8.3. Usually 10 to 60 mL, typically 25 to 55mL, more typically 40 to 50 mL, most typically approximately 45 mL of chilled carbonated mineral water per liter of water is used. Usually the chilled carbonated mineral water is at a temperature of 0 to 25° C., 0 to 20° C., 0.5 to 25° C., 0.5 to 20° C., 0.5 to 15° C., 0.5 to 10° C., 0.5 to 9° C., 0.5 to 8° C., 0.5 to 7° C., 1 to 20° C., 1 to 15° C., 1 to 10° C., 1.5 to 20° C., 1.5 to 15° C., 1.5 to 10° C., 2 to 20° C., 2 to 15° C., 2 to 10° C., 3 to 20° C., 3 to 15° C., 4 to 20° C., 4 to 15° C., 4 to 10° C., 5 to 20° C., 5 to 15° C., 6 to 20° C., 6 to 15° C., 6 to 10° C., 7 to 20° C., 7 to 15° C., 7 to 10° C., 8 to 20° C., 8 to 15° C., 8 to 10° C., 9 to 20° C., 9 to 15° C., 9 to 10° C., 10 to 15° C., typically 0 to 15° C., more typically 0 to 10° C., even more typically 3° C. to 10° C., most typically 5° C. to 10° C. and even most typically 5° C. Alternatively the metal carbonate or metal carbonate hydroxide or metal oxide or mixture thereof can be added after the carbon dioxide has been added.

Generally the metal bicarbonate in aqueous solution may be derived from a metal carbonate or metal carbonate hydroxide or metal oxide or metal bicarbonate or metal hydroxide or other appropriate metal compound or any mixture thereof. Examples include magnesium, sodium, potassium, calcium, lithium carbonate or carbonate hydroxide or oxide or bicarbonate or a mixture of any two or more thereof. For example magnesium carbonate hydroxide pentahydrate, the calcite series or dolomite series of minerals $(Mg, Ca)CO_3$ or limestone or dolomite rocks is used. Generally magnesium carbonate hydroxide pentahydrate or a mixture of magnesium carbonate hydroxide pentahydrate and sodium bicarbonate is used.

Generally the pH of the aqueous metal bicarbonate solution for oral administration is neutral to mildly alkaline, typically in the range pH 7 to 9 or pH 7 to 8.6, more typically pH 7.5 to 8.8 or pH 7.5 to 8.5 or pH 7.8 to 8.6, pH 7.8 to 8.5, pH 7.8 to 8.4, pH 7.8 to 8.3, pH 7.8 to 8.2, pH 7.8 to 8.1, pH 7.8 to 8.0, pH 7.8 to 7.9, pH 7.9 to 8.6, pH 7.9 to 8.5, pH 7.9 to 8.4, pH 7.9 to 8.3, pH 7.9 to 8.2, pH 7.9 to 8.1, pH 7.9 to 8.0, pH 8.0 to 8.6, pH 8.0 to 8.5, pH 8.0 to 8.4, pH 8.0 to 8.3, pH 8.0 to 8.2, pH 8.0 to 8.1, pH 8.1 to 8.6, pH 8.1 to 8.5, pH 8.0 to 8.4, pH 8.1 to 8.3, pH 8.1 to 8.2, pH 8.2 to 8.6, pH 8.2 to 8.5, pH 8.2 to 8.4, pH 8.2 to 8.3, pH 8.3 to 8.6, pH 8.3 to 8.5, pH 8.3 to 8.4, pH 8.4 to 8.6, pH 8.4 to 8.5, pH 8.5 to 8.6, even more typically pH 8 to 8.5 or pH 8.2 to 8.6, most typically pH 8.3. Generally the pH of the aqueous metal bicarbonate solution for parenteral administration is neutral to very mildly alkaline, typically in the range pH 7 to 7.6, or pH 7.0 to 7.5, or pH 7.1 to 7.5, more typically pH 7.2 to 7.5 or pH 7.3 to 7.5 or pH 7.4 to 7.5. Generally the aqueous neutral to mildly alkaline metal bicarbonate solution is prepared and stored at a temperature ranging from 0 to 25° C., 0 to 20° C., 0.5 to 25° C., 0.5 to 20° C., 0.5 to 15° C., 0.5 to 10° C., 0.5 to 9° C., 0.5 to 8° C., 0.5 to 7° C., 1 to 20° C., 1 to 15° C., 1 to 10° C., 1.5 to 20° C., 1.5 to 15° C., 1.5 to 10° C., 2 to 20° C., 2 to 15° C., 2 to 10° C., 3 to 20° C., 3 to 15° C., 4 to 20° C., 4 to 15° C., 4 to 10° C., 5 to 20° C., 5 to 15° C., 6 to 20° C., 6 to 15° C., 6 to 10° C., 7 to 20° C., 7 to 15° C., 7 to 10° C., 8 to 20° C., 8 to 15° C., 8 to 10° C., 9 to 20° C., 9 to 15° C., 9 to 10° C., 10 to 15° C., typically 0 to 15° C., more typically 0 to 10° C., even more typically 3° C. to 10° C., most typically 5° C. to 10° C. and even most typically 5° C.

Generally the pH adjusting agent is carbon dioxide gas, carbonic acid in water, hydrated carbon dioxide in water, carbon dioxide gas in water, carbonated soft drinks, carbonated mineral water, soda water or other carbon dioxide-containing-aqueous diluents or an alkali or any mixture thereof. Examples of alkalis are water soluble drinkable alkalis such as sodium hydroxide, sodium carbonate, potassium carbonate or potassium hydroxide or any mixture thereof.

Typically additives may be added during the process of the invention or to the aqueous neutral to mildly alkaline metal bicarbonate solution. The additives may be 0 mg or 0.5 mg to 1000 mg sodium bicarbonate per liter of aqueous neutral to mildly alkaline metal bicarbonate solution, typically 25 mg to 900 mg per liter of aqueous neutral to mildly alkaline metal bicarbonate solution, typically 50 mg to 800 mg or 50 mg to 500 mg per liter of aqueous neutral to mildly alkaline metal bicarbonate solution, more typically 100 mg to 700 mg per liter of aqueous neutral to mildly alkaline metal bicarbonate solution, even more typically 200 mg to 600 mg per liter of aqueous neutral to mildly alkaline metal bicarbonate solution, most typically 300 mg to 500 mg per liter of aqueous neutral to mildly alkaline metal bicarbonate solution, even most typically 500 mg per liter of aqueous neutral to mildly alkaline metal bicarbonate solution. The additives may also be chlorides and other appropriate salts of magnesium, sodium, potassium, calcium and lithium, such as carbonates or hydroxides or sulfates, with or without the addition of sodium bicarbonate. For example, magnesium sulfate, magnesium chloride or other soluble salts of magnesium. Further additives may include potassium bicarbonate, calcium bicarbonate or lithium bicarbonate. Generally calcium bicarbonate is prepared by adding carbonic acid or carbonated water or hydrated carbon dioxide or carbon dioxide gas to a mixture of calcium carbonate in water. Generally lithium bicarbonate is prepared by adding carbonic acid and/or carbonated water and/or hydrated carbon dioxide and/or carbon dioxide gas and/or solid carbon dioxide to a mixture of lithium carbonate in water.

The aqueous neutral to mildly alkaline metal bicarbonate solution may further include a stabilising agent. The stabilising agent may also be a pH adjusting agent. Typically the stabilising agent is a gaseous phase, for example carbon dioxide gas, which maintains and/or stabilises the solution at a pH of 7 to 9 and at a temperature of 0 to 55° C. more typically 0 to 25° C.

Generally once the solution is prepared, the solution may be stored under a blanket of carbon dioxide gas or a mixture of carbon dioxide gas and a nondeleterious inert gas, for example, argon, helium, air, oxygen and/or nitrogen wherein the amount of carbon dioxide present in the inert gas is sufficient to maintain the solution at a pH of 7 to 9 and at a temperature of 0 to 25° C. and to prevent the metal bicarbonate from forming insoluble compounds which can precipitate out of solution. Typically the carbon dioxide gas above the solution prevents loss of carbon dioxide from the solution. The amount of carbon dioxide in the gaseous mixture provides partial pressure on the liquid which is substantially equal to the partial pressure which is produced from equilibrium of bicarbonate in the solution at the mixing temperature.

Magnesium Bicarbonate Particularly

Typically the production of magnesium bicarbonate utilises the dissolution of magnesium carbonate by carbonic acid or hydrated carbon dioxide solutions. Ideally, the dissolution is produced within a defined range of conditions—a defined range of pH values, a defined range of temperature values and a defined minimum time. For optimal biological and medical activities, and for therapeutic safety, the concentrations of the component ions are defined also.

Typically to prepare the aqueous neutral to mildly alkaline metal bicarbonate solution, crushed or powdered metal carbonate, or metal carbonate hydroxide or metal oxide, such as magnesium carbonate $MgCO_3$, or commercial magnesium carbonate hydroxide pentahydrate $(MgCO_3)_4.Mg(OH)_2.5H_2O$, or other commercial magnesium carbonate hydroxides, or hydrated magnesium oxides, or magnesium oxides heated with carbon dioxide, or the calcite series or dolomite series of minerals $(Mg, Ca)CO_3$, or limestone or dolomite rocks is mixed with water. A cloudy suspension is obtained. Sufficient carbonic acid and/or hydrated carbon dioxide and/or carbon dioxide gas and/or solid carbon dioxide is added to obtain a solution having a pH 7 to 9 or pH 7 to 8.6, more typically pH 7.5 to 8.8 or pH 7.5 to 8.5 or pH 7.8 to 8.6, pH 7.8 to 8.5, pH 7.8 to 8.4, pH 7.8 to 8.3, pH 7.8 to 8.2, pH 7.8 to 8.1, pH 7.8 to 8.0, pH 7.8 to 7.9, pH 7.9 to 8.6, pH 7.9 to 8.5, pH 7.9 to 8.4, pH 7.9 to 8.3, pH 7.9 to 8.2, pH 7.9 to 8.1, pH 7.9 to 8.0, pH 8.0 to 8.6, pH 8.0 to 8.5, pH 8.0 to 8.4, pH 8.0 to 8.3, pH 8.0 to 8.2, pH 8.0 to 8.1, pH 8.1 to 8.6, pH 8.1 to 8.5, pH 8.1 to 8.4, pH 8.1 to 8.3, pH 8.1 to 8.2, pH 8.2 to 8.6, pH 8.2 to 8.5, pH 8.2 to 8.4, pH 8.2 to 8.3, pH 8.3 to 8.6, pH 8.3 to 8.5, pH 8.3 to 8.4, pH 8.4 to 8.6, pH 8.4 to 8.5, pH 8.5 to 8.6, even more typically pH 8 to 8.6 or pH 8.2 to 8.6, most typically pH 8.3. The solution is then typically placed in a closed or sealed container at 0 to 20° C. or 0 to 15° C. with occasional mixing until a clear solution develops. The amount of carbonic acid and/or hydrated carbon dioxide and/or carbon dioxide gas bubbled through the solution and dissolved therein and/or solid carbon dioxide is sufficient to prevent precipitation of water insoluble metal compounds (such as magnesium or calcium carbonate). A clear solution is generally obtained in about 6 hours to 7 days, typically 12 hours to 5 days, more typically 24 hours to 5 days, most typically 24 hours to 3 days. Generally the aqueous neutral to mildly alkaline metal bicarbonate solution is prepared and stored at a temperature ranging from 0 to 55° C., 0 to 25° C., 0 to 20° C., 0.5 to 25° C., 0.5 to 20° C., 0.5 to 15° C., 0.5 to 10° C., 0.5 to 9° C., 0.5 to 8° C., 0.5 to 7° C., 1 to 20° C., 1 to 15° C., 1 to 10° C., 1.5 to 20° C., 1.5 to 15° C., 1.5 to 10° C., 2 to 20° C., 2 to 15° C., 2 to 10° C., 3 to 20° C., 3 to 15° C., 4 to 20° C., 4 to 15° C., 4 to 10° C., 5 to 20° C., 5 to 15° C., 6 to 20° C., 6 to 15° C., 6 to 10° C., 7 to 20° C., 7 to 15° C., 7 to 10° C., 8 to 20° C., 8 to 15° C., 8 to 10° C., 9 to 20° C., 9 to 15° C., 9 to 10° C., 10 to 15° C., typically 0 to 15° C., more typically 0 to 10° C., even more typically 3° C. to 10° C., most typically 5° C. to 10° C. and even most typically 5° C. Alternatively the crushed or powdered metal carbonate, or metal carbonate hydroxide or metal oxide or mixture thereof is added to an aqueous solution of the carbonic acid and/or hydrated carbon dioxide and/or to an aqueous solution through which carbon dioxide gas is bubbled and/or solid carbon dioxide has been added. The amount of carbonic acid and/or hydrated carbon dioxide and/or carbon dioxide gas bubbled through the solution and dissolved therein and/or solid carbon dioxide is sufficient to prevent precipitation of water insoluble metal compounds (such as magnesium or calcium carbonate).

Typically one liter of water is placed in a container and sufficient carbonic acid and/or carbonated water and/or hydrated carbon dioxide and/or carbon dioxide gas and/or solid carbon dioxide is added to produce a pH value of approximately pH 5.2. (In practice, approximately 40 to 45 mL of chilled (5° C.) carbonated mineral water is used depending on the initial pH of the water). The container is sealed and the contents are mixed. 485 mg magnesium carbonate hydroxide pentahydrate powder $(MgCO_3)_4.Mg(OH)_2.5H_2O$, molecular weight 485 is added. The container is again sealed and the contents are mixed.

The container is stored at a temperature of 0 to 10° C. and the contents mixed regularly. Sufficient time is allowed for a clear solution of magnesium bicarbonate to develop at a range of pH 8.0 to pH 8.6, preferably pH 8.3. This takes approximately 24 to 72 hours. Alternatively the carbonic acid and/or carbonated water and/or hydrated carbon dioxide and/or carbon dioxide gas and/or solid carbon dioxide is added to the magnesium carbonate hydroxide pentahydrate powder in water. Alternatively one liter of water is placed in a container and sufficient carbonic acid and/or carbonated water and/or hydrated carbon dioxide and/or solid carbon dioxide is added to produce a pH value less than pH 5.2. (In practice, approximately 30 mL to 40 mL of chilled water is used depending on the initial pH of the water). The container is sealed and the contents are mixed. 485 mg magnesium carbonate hydroxide pentahydrate powder $(MgCO_3)_4.Mg(OH)_2.5H_2O$, molecular weight 485 is added. The container is again sealed and the contents are mixed. The container is stored at a temperature of 0 to 10° C. and the contents mixed regularly. The pH of the water is then adjusted with an alkali such as sodium hydroxide or potassium hydroxide to a pH of 8 to 8.6, typically pH 8.3. Alternatively the carbonic acid or carbonated water and/or hydrated carbon dioxide and/or carbon dioxide gas and/or solid carbon dioxide is added to the magnesium carbonate hydroxide pentahydrate powder in water.

The above processes may optionally be conducted under an atmosphere of carbon dioxide or a gas comprising carbon dioxide.

Generally once the solution is prepared, it may be stored under a blanket of carbon dioxide gas to maintain the solution at a pH of 7 to 9 and at a temperature of 0 to 25° C. Usually one liter of the magnesium bicarbonate solution prepared above contains approximately 120 mg of magnesium per liter of aqueous neutral to mildly alkaline metal bicarbonate solution and approximately 600 mg of bicarbonate. 500 mg sodium bicarbonate (or potassium bicarbonate) is added to the magnesium bicarbonate solution and mixed. The mixture is stored in a sealed container in a refrigerator. The mixture contains approximately 120 mg magnesium per liter of aqueous neutral to mildly alkaline metal bicarbonate solution, 135 mg sodium per liter of aqueous neutral to mildly alkaline metal bicarbonate solution and 950 mg bicarbonate per liter of aqueous neutral to mildly alkaline metal bicarbonate solution.

Generally the aqueous neutral to mildly alkaline metal bicarbonate solution of the invention is administered or consumed orally. Typically the solution is an orally drinkable solution. Typically the solution is a therapeutic orally drinkable solution. Alternatively a gelling agent may added to the solution and the solution subjected to gelling conditions to gel the solution and the resultant gel may be consumed orally. For example, the aqueous neutral to mildly alkaline metal bicarbonate solution may be prepared as a solution or an iced confectionary, such as an ice block or iced dessert, which is ingested orally. Alternatively the aqueous neutral to mildly alkaline metal bicarbonate solution may be prepared in the form of a tablet, lozenge or lolly which is ingested orally. For example, the aqueous neutral to mildly alkaline metal bicarbonate solution may be administered for metabolic acidosis or renal failure. Optionally the solution may be sterilised. Typically the aqueous neutral to mildly alkaline metal bicarbonate solution is prepared as a solution which is ingested on a regular basis hourly, daily, monthly or yearly. The amount and frequency of aqueous neutral to mildly alkaline metal bicarbonate solution administered/consumed in a day is generally sufficient so as to maintain a steady bicarbonate level in the bicarbonate concentration of a taker's body fluids. It is preferable to avoid a rapid increase in the bicarbonate level in the bicarbonate concentration of a taker's body fluids. The amount of aqueous neutral to mildly alkaline metal bicarbonate solution administered in a day ranges from 250 mL to 6 liters, typically 250 mL to 5.5 liters, 250 mL to 5 liters, 250 mL to 4.5 liters, 250 mL to 4 liters, 250 mL to 3.5 liters, 250 mL to 3 liters, 500 mL to 6 liters, 500 mL to 5.5 liters, 500 mL to 5 liters, 500 mL to 4.5 liters, 500 mL to 4 liters, 500 mL to 3.5 liters, 500 mL to 3 liters, more typically 1 liter to 6 liters, 1 liter to 5.5 liters, 1 liter to 5 liters, 1 liter to 4.5 liters, 1 liter to 4 liters, 1 liter to 3.5 liters, even more typically 1 liter to 3 liters, 1.5 liters to 6 liters, 1.5 liters to 5.5 liters, 1.5 liters to 5 liters, 1.5 liters to 4.5 liters, 1.5 liters to 4 liters, 1.5 liters to 3.5 liters, 1.8 liters to 3.3 liters, 1.8 to 2.8 liters, 1.8 to 2.5 liters, 1.8 to 2.3 liters, 1.8 to 2.0 liters, most typically 2 to 3 liters, typically 2.3 to 2.8 liters, more typically 2.3 to 2.6 liters, usually 2.1 to 3 liters. The aqueous neutral to mildly alkaline metal bicarbonate solution may be administered on a full or empty stomach, typically the aqueous neutral to mildly alkaline metal bicarbonate solution is administered on an empty stomach. Usually 1.5 to 3.5 liters, typically 1.8 to 3 liters, more typically 1.5 to 2.4 liters, even more typically 1.8 to 2.1 liters and usually between 1.8 and 2.7 liters of aqueous neutral to mildly alkaline metal bicarbonate solution is ingested, administered or consumed on an empty stomach by a mammal (typically a human) in equal or non equal volume amounts (100 mL–1000 mL, 200–800 mL, 250–750 mL, 275–700 mL, 300–650 mL, 350–600 mL, 400–550 mL, 450–500 mL, typically about 300–400 mL, more typically about 375 mL volume amounts a number of times (typically at set times) each day for the required number of times per day to drink the desired daily amount of the solution). For example if 1800 mL per day is to be consumed then a user may drink six 300 mL amounts of the solution every 2 to 2.5 hours throughout the day. The oral consumption of the solution three or more times at roughly equally spaced apart intervals throughout the day is more desirable than consuming the solution in one or two lots throughout the day. The idea of taking the solution is to take it regularly throughout the day so that a simulated continuous oral intake or a close to continuous regular oral intake of the solution occurs. Thus depending on the condition and the subject one suitable administration/consumption regime could be nine by 200 mL amounts of the solution, each 200 mL amount being orally administered/consumed about every 1.5–1.75 hours to provide a total daily intake of 1800 mL. Alternatively, once again depending on the condition and the subject one suitable administration/consumption regime could be nine by 300 mL amounts of the solution, each 300 mL amount being orally administered/consumed about every 1.5–1.75 hours to provide a total daily intake of 2700 mL. Alternatively, once again depending on the condition and the subject one suitable administration/consumption regime could be nine by 350 mL amounts of the solution, each 350 mL amount being orally administered/consumed about every 1.5–1.75 hours to provide a total daily intake of 3150 mL. Typically the solution is administered/consumed 3 to 30, 3–25, 3–20, 3–15, 3–12, 3–10, 3–9, 3–8, 3–7, 3–6, 3–5, 3–4, 4–30, 4–25, 4–20, 4–15, 4–12, 4–10, 4–9, 4–8, 4–7, 4–6, 4–5, 5–30, 5–25, 5–20, 5–15, 5–12, 5–11, 5–10, 5–9, 5–8, 5–7, 5–6, 6–30, 6–25, 6–20, 6–15, 6–12, 6–11, 6–10, 6–9, 6–8, 6–7, 7–30, 7–25, 7–20, 7–15, 7–12, 7–11, 7–10, 7–9, 7–8, 8–30, 8–25, 8–20, 8–15, 8–12, 8–11, 8–10, 8–9 times per day at regular or irregular intervals or a mixture of both regular and irregular intervals, throughout each day. Typically the solution is administered/consumed every 0.3–10, 0.3–8, 0.3–7, 0.3–6, 0.3–5, 0.3–4.5, 0.3–4, 0.3–3.5, 0.3–3, 0.3–2.5, 0.3–2, 0.3–1.5, 0.3–1, 0.3–0.75, 0.3–0.5 hours/day when the subject is awake. More typically the solution is administered/consumed every 0.5–8, 0.5–7, 0.5–6, 0.5–5, 0.5–4.5, 0.5–4, 0.5–3.5, 0.5–3, 0.5–2.5, 0.5–2, 0.5–1.5, 0.5–1, 0.5–0.8, 0.5–0.75 hours/day when the subject is awake. Where possible the solution is consumed/administered on an empty (e.g. before eating). The solution may be administered according to these latter dosages over short (for example 1 to 60 days, 10 to 40 days, 3 months to 6 months, 1 day to 6 months) or long (for example 6 months to 10 years or more, 9 months to 1 8 months, 1 year to 3 years, 1 year to 5 years, 2 to 6 years) periods as required. Usually the amount of aqueous neutral to mildly alkaline metal bicarbonate solution administered to a mammal is 5 to 100 mL per Kg, more usual 10 to 50 mL per Kg, most usual 14 to 29 mL per Kg or 25 to 43 mL per Kg.

The solution may include other additives such as sweeteners, preservatives, flavourings and other suitable additives. Examples of suitable sweetners include sucrose, lactose, glucose, aspartame or saccharine. Examples of suitable flavouring agents include peppermint oil, oil of wintergreen, cherry, orange or raspberry flavouring. Examples of suitable preservatives include sodium benzoate, vitamin E, alpha-tocopherol, ascorbic acid, methyl paraben, propyl paraben or sodium bisulphite.

Typically the aqueous neutral to mildly alkaline metal bicarbonate solution is orally administered/consumed on an empty stomach. Usually consumption in this manner avoids the mixing of bicarbonate anions with stomach acid which may result in the loss of bicarbonate. Usually the aqueous neutral to mildly alkaline metal bicarbonate solution is consumed in small amounts a number of times through a day typically at set times each day to avoid a rapid increase in the bicarbonate concentration of body fluids. Usually the amount of aqueous neutral to mildly alkaline metal bicarbonate solution consumed at commencement is 500 mL per day and is increased by increments over a period of one month to the maximum consumption. This start-up schedule generally avoids any gastrointestinal side effects due to the smooth muscle relaxation properties of magnesium.

The aqueous neutral to very mildly alkaline metal bicarbonate solution of the invention may be administered intravenously (e.g. by discrete injection, semi continuous injection or drip feed or continuous injection or drip feed) or by other parenteral routes. Another embodiment of the invention is directed to a pharmaceutical composition comprising the solution of the first or eleventh embodiments together with one or more pharmaceutically acceptable carriers, diluents, adjuvants and/or excipients. Typically the pharmaceutical composition is suitable for oral or parenteral administration. Another embodiment of the invention is directed to a veterinary composition comprising the solution of the first or eleventh embodiments together with one or more veterinarily acceptable carriers, diluents, adjuvants and/or excipients. Typically the veterinary composition is suitable for oral or parenteral administration. The amount and frequency of aqueous neutral to mildly alkaline metal bicarbonate solution administered/consumed in a day is generally sufficient so as to maintain a steady bicarbonate level in the bicarbonate concentration of a taker's body fluids. It is preferable to avoid a rapid increase in the bicarbonate level in the bicarbonate concentration of a talker's body fluids. For parenteral administration, the solution is generally sterile. Suitable mono-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents. Suitable buffering agents include sodium borate, sodium acetate, sodium citrate, or sodium tartrate, for example. Typically the solution is administered on a regular basis throughout a day to a patient requiring treatment. For example a patient may be parenterally administered the solution by way of a continuous drip feed or alternatively by way of a number of injections of the solution throughout a day (e.g. every 0.5–8 hours, more typically every 1–4 hours). The treatment is generally continued as long as required to alleviate the patient's symptons to a satisfactory level. For concentration of metal bicarbonate in the compositions, frequency of administration and amount administered see discussion under oral administration.

BEST MODE AND OTHE MODE(S) FOR CARRYING OUT THE INVENTION

Figure 1:
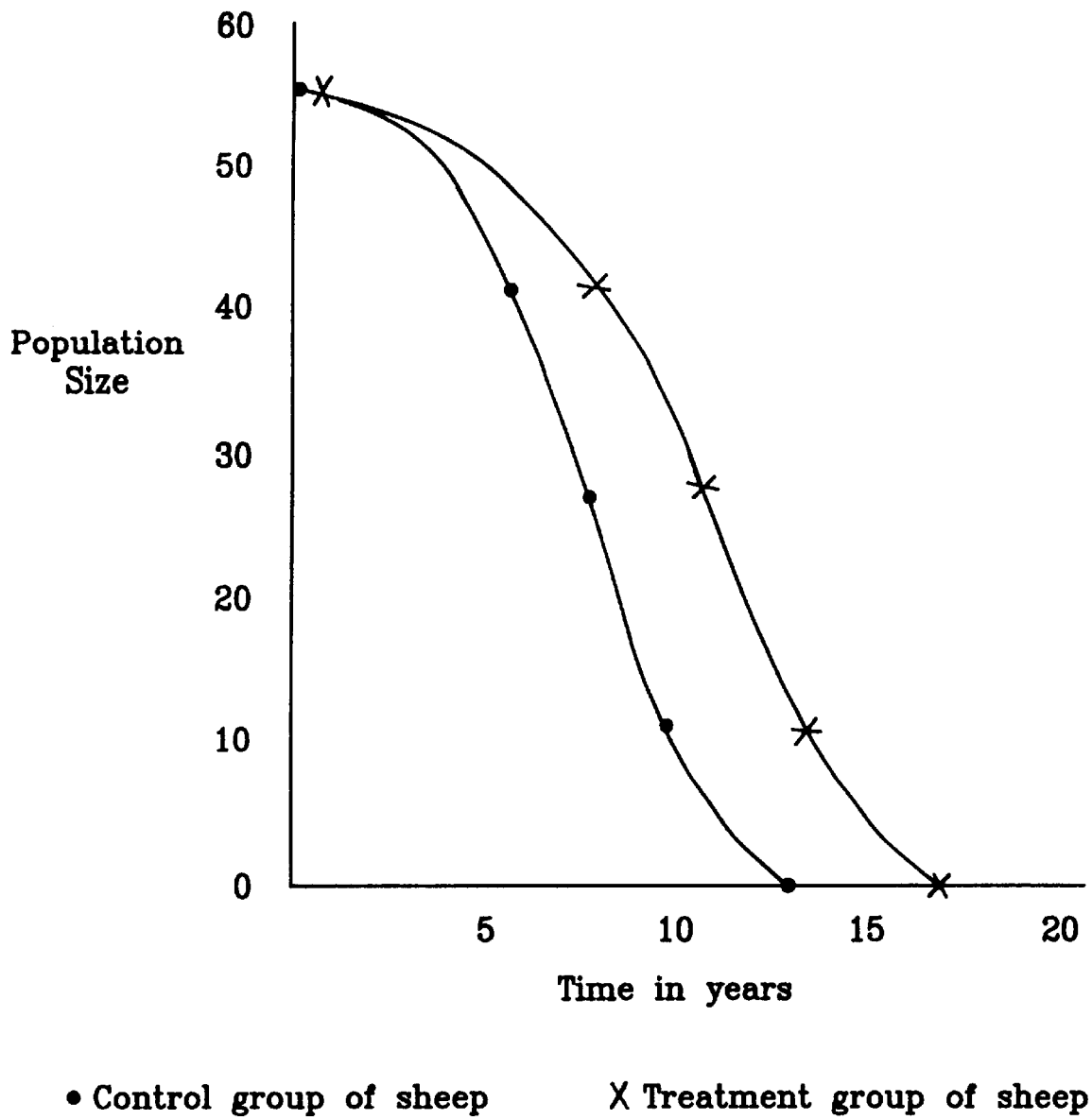
FIG. 1 are plots of the survival curves for a control group of sheep and a treatment group of sheep.

Magnesium bicarbonate is a natural hydrated salt which exists only in an aqueous solution. It may be formed in spring water by an ion exchange process between the protons in carbonic acid (formed from the hydration of carbon dioxide located in the atmosphere, organic material, soils and rocks) and the magnesium in the constituent minerals of rocks (particularly the ferromagnesian minerals known as pyroxene and olivine that constitute basalt rocks).

The ion exchange process can be represented by the following equations:

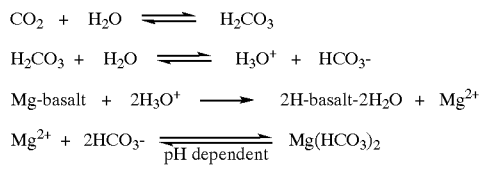

The term magnesium bicarbonate is used universally to describe the mixture of magnesium cations and bicarbonate anions found in spring waters and mineral waters. Most spring waters and mineral waters have acidic pH values (about pH 6.0). If the pH value of the water rises (due to contact with hydroxides), the magnesium cations and bicarbonate anions "attract" each other (reversibly) to form the true salt. The chemical formula of magnesium bicarbonate may be written as $Mg(HCO_3)_2$, or (more accurately) $Mg(H_2O)_4(HCO_3)_2$. This latter formula takes into account the hexahydrated magnesium cation $Mg(H_2O)_6^{2+}$.

In essence, magnesium bicarbonate exists in aqueous solution probably as an hydrated salt of indeterminate hydration size due to the hydrogen bonds between linked water dipoles centred around the hydrated magnesium cation.

The chemical processes occurring in magnesium bicarbonate solutions are complex and depend on the concentrations of magnesium cations and other ions. The following reactions are considered to occur:

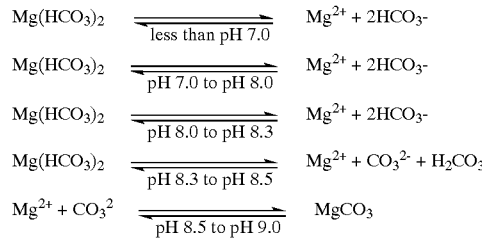

There exists also a range of possible acid-base equilibria involving $HCO_3^-$, $H_3O^+$, $CO_3^{2-}$ and $OH^-$ ions and $CO_2$ and $H_2CO_3$. Usually the pH adjusting agent (and/or stabilising agent) maintains the acid-base equilibria.

Typically to prepare the aqueous neutral to mildly alkaline metal bicarbonate solution, crushed or powdered metal carbonate, or metal carbonate hydroxide or metal oxide, such as magnesium carbonate $MgCO_3$, or commercial magnesium carbonate hydroxide pentahydrate $(MgCO_3)_4.Mg(OH)_2.5H_2O$, or other commercial magnesium carbonate hydroxides, or hydrated magnesium oxides, or magnesium oxides heated with carbon dioxide, or the calcite series or dolomite series of minerals $(Mg, Ca)CO_3$, or limestone or dolomite rocks is mixed with water. A cloudy suspension is obtained. Sufficient carbonic acid or hydrated carbon dioxide or carbon dioxide gas is added to obtain a solution having a pH 7 to 9 or pH 7 to 8.6, more typically pH 7.5 to 8.8 or pH 7.5 to 8.5 or pH 7.8 to 8.6, pH 7.8 to 8.5, pH 7.8 to 8.4, pH 7.8 to 8.3, pH 7.8 to 8.2, pH 7.8 to 8.1, pH 7.8 to 8.0, pH 7.8 to 7.9, pH 7.9 to 8.6, pH 7.9 to 8.5, pH 7.9 to 8.4, pH 7.9 to 8.3, pH 7.9 to 8.2, pH 7.9 to 8.1, pH 7.9 to 8.0, pH 8.0 to 8.6, pH 8.0 to 8.5, pH 8.0 to 8.4, pH 8.0 to 8.3, pH 8.0 to 8.2, pH 8.0 to 8.1, p H 8.1 to 8.6, p H 8.1 to 8.5, pH 8.1 to 8.4, pH 8.1 to 8.3, pH 8.1 to 8.2, pH 8.2 to 8.6, pH 8.2 to 8.5, pH 8.2 to 8.4, pH 8.2 to 8.3, pH 8.3 to 8.6, pH 8.3 to 8.5, pH 8.3 to 8.4, pH 8.4 to 8.6, pH 8.4 to 8.5, pH 8.5 to 8.6, even more typically pH 8 to 8.5 or pH 8.2 to 8.6, most typically pH 8.3. The solution is then typically placed in a sealed container at 0 to 20° C. with occasional mixing until a clear solution develops. A clear solution is generally obtained in about 6 hours to 7 days, typically 12 hours to 5 days, more typically 24 hours to 5 days, most typically 24 hours to 3 days. Generally the aqueous neutral to mildly alkaline metal bicarbonate solution is prepared and stored at a temperature ranging from 0 to 25° C., 0 to 20° C., 0.5 to 25° C., 0.5 to 20° C., 0.5 to 15° C., 0.5 to 10° C., 0.5 to 9° C., 0.5 to 8° C., 0.5 to 7° C., 1 to 20° C., 1 to 15° C., 1 to 10° C., 1.5 to 20° C., 1.5 to 15° C., 1.5 to 10° C., 2 to 20° C., 2 to 15° C., 2 to 10° C., 3 to 20° C., 3 to 15° C., 4 to 20° C., 4 to 15° C., 4 to 10° C., 5 to 20° C., 5 to 15° C., 6 to 20° C., 6 to 15° C., 6 to 10° C., 7 to 20° C., 7 to 15° C., 7 to 10° C., 8 to 20° C., 8 to 15° C., 8 to 10° C., 9 to 20° C., 9 to 15° C., 9 to 10° C., 10 to 15° C., typically 0 to 15° C., more typically 0 to 10° C., even more typically 3° C. to 10° C., most typically 5° C. to 10° C. and even most typically 5° C. Alternatively the crushed or powdered metal carbonate, or metal carbonate hydroxide or metal oxide or mixture thereof is added to an aqueous solution of the carbonic acid or hydrated carbon dioxide or carbon dioxide gas.

Typically one liter of water is placed in a container and sufficient carbonic acid or carbonated water or hydrated carbon dioxide or carbon dioxide gas is added to produce a pH value of approximately pH 5.2. (In practice, approximately 40 to 45 mL of chilled (5° C.) carbonated mineral water is used depending on the initial pH of the water). The container is sealed and the contents are mixed. 485 mg magnesium carbonate hydroxide pentahydrate powder $(MgCO_3)_4 \cdot Mg(OH)_2 \cdot 5H_2O$, molecular weight 485 is added. The container is again sealed and the contents are mixed. The container is stored at a temperature of 0 to 10° C. and the contents mixed regularly. Sufficient time is allowed for a clear solution of magnesium bicarbonate to develop at a range of pH 8.0 to pH 8.5, typically pH 8.3. This takes approximately 24 to 72 hours. Alternatively the carbonic acid or carbonated water or hydrated carbon dioxide or carbon dioxide gas is added to the magnesium carbonate hydroxide pentahydrate powder in water.

Alternatively one liter of water is placed in a container and sufficient carbonic acid or carbonated water or hydrated carbon dioxide gas is added to produce a pH value less than pH 5.2. (In practice, approximately 30 mL to 40 mL of chilled water is used depending on the initial pH of the water). The container is sealed and the contents are mixed. 485 mg magnesium carbonate hydroxide pentahydrate powder $(MgCO_3)_4 \cdot Mg(OH)_2 \cdot 5H_2O$, molecular weight 485 is added. The container is again sealed and the contents are mixed. The container is stored at a temperature of 0 to 10° C. and the contents mixed regularly. The pH of the water is then adjusted with an alkali such as sodium hydroxide or potassium hydroxide to a pH of 8 to 8.5, typically pH 8.3. Alternatively the carbonic acid or carbonated water or hydrated carbon dioxide or carbon dioxide gas is added to the magnesium carbonate hydroxide pentahydrate powder in water.

Generally once the solution is prepared, the solution may be stored in a closed container under a blanket of carbon dioxide gas or a mixture of carbon dioxide gas and usually a nondeleterious inert gas, for example, argon, helium and/or nitrogen to maintain the solution at a pH of 7 to 9 and at a temperature of 0 to 25° C. and at 0.8 to 5 atm. The carbon dioxide gas blanket prevents loss of carbon dioxide from the solution. The amount of carbon dioxide in the gaseous mixture provides partial pressure on the liquid which is substantially equal to the partial pressure of carbon dioxide from carbon dioxide from the solution which is produced from equilibrium of bicarbonate in the solution at the particular temperature. In this way the solution is stabilised. If the solution were left in an open container for any substantial length of time precipitation of metal carbonate from the solution would occur as a result of decomposition of the bicarbonate in the solution as carbon dioxide is liberated from the solution. By using a stabilising agent in and/or above the solution such decomposition is substantially miniimised or prevented. Alternatively the solution may be stored in a closed or sealed container (generally airtight) which is substantially filled with the solution whereby there is substantially no gas in the container or little gas compared to the amount of liquid in the container.

The relevant chemical reactions may be represented by the following equations:

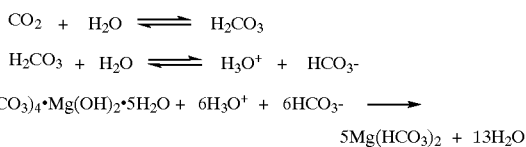

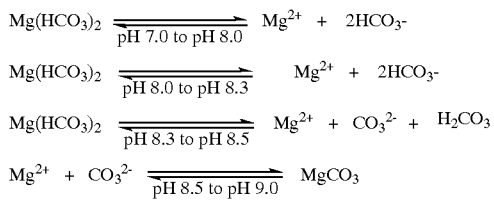

Usually one liter of the magnesium bicarbonate solution prepared above contains approximately 120 mg of magnesium per liter of aqueous neutral to mildly alkaline metal bicarbonate solution and approximately 600 mg of bicarbonate. 500 mg sodium bicarbonate (or potassium bicarbonate) is added to the magnesium bicarbonate solution and mixed. The mixture is stored in a sealed container in a refrigerator. The mixture contains approximately 120 mg magnesium per liter of aqueous neutral to mildly alkaline metal bicarbonate solution, 135 mg sodium per liter of aqueous neutral to mildly alkaline metal bicarbonate solution and 950 mg bicarbonate per liter of aqueous neutral to mildly alkaline metal bicarbonate solution.

In the body, normal intracellular pH value is pH 7.2. Under acidic conditions, such as adenosine triphosphate (ATP) hydrolysis, intracellular pH value may decrease to pH 6.5. In practice, a pH value is chosen for bicarbonate solutions that exceeds normal blood plasma pH value (pH>7.38).

A low temperature, between 0 and 10° C., typically 5 to 10° C., ensures that carbon dioxide stays dissolved in solution to maximise carbon dioxide hydration. Above 15 to 20° C., the solubility of carbon dioxide is low, the carbon dioxide leaves the solution, and particles and sediments may occur in the solution. Above 15 to 20° C., the solution may be cloudy in appearance.

At high magnesium concentrations, a minimum time, at least 24 to 72 hours at 5° C., is required for completion of the kinetic processes that produce a clear solution of magnesium bicarbonate. (The kinetic processes include the hydration of carbon dioxide, the dissolution of magnesium carbonate and the dissolution of magnesium hydroxide.) The concentration of magnesium cations (in association with bicarbonate anions) is generally in the range 25 mg to 250 mg per liter aqueous neutral to mildly alkaline metal bicarbonate solution (depending on the pH value of the metal bicarbonate solution). Usually the maximum magnesium concentration that can be maintained in solution as magnesium bicarbonate may be approximately 120 mg per liter aqueous neutral to mildly alkaline metal bicarbonate solution at pH 8.3. As the pH value decreases, the concentration of magnesium that can be maintained in solution increases. Because magnesium chloride is soluble, higher concentrations of magnesium can be maintained in solution if chlorides (such as sodium chloride) are added to the aqueous neutral to mildly alkaline metal bicarbonate solution.

The solubility product constant for magnesium carbonate, is reported to be approximately $3.5 \times 10^{-8}$. The solubility product constant for magnesium hydroxide is reported to be approximately $1.1 \times 10^{-11}$. Calculated from these values, the maximum concentrations of magnesium cations that can exist in solution as carbonates or hydroxides are approximately 20 mg per liter aqueous metal bicarbonate solution and 10 mg per liter aqueous neutral to mildly alkaline metal bicarbonate solution respectively.

Generally the aqueous neutral to mildly alkaline metal bicarbonate solution of the invention is administered or consumed orally. Typically the solution is an orally drinkable solution. Typically the solution is a therapeutic orally drinkable solution. For example, the aqueous neutral to mildly alkaline metal bicarbonate solution may be prepared as a solution or an iced confectionary, such as an ice block or iced dessert, which is ingested orally. Alternatively the aqueous neutral to mildly alkaline metal bicarbonate solution may be prepared in the form of a tablet, lozenge or lolly which is ingested orally. For example, the aqueous neutral to mildly alkaline metal bicarbonate solution may be administered for metabolic acidosis or renal failure. Optionally the solution may be sterilised. Typically the aqueous neutral to mildly alkaline metal bicarbonate solution is prepared as a solution which is ingested hourly, daily, monthly or yearly. The amount of aqueous neutral to mildly alkaline metal bicarbonate solution administered in a day ranges from 250 mL to 6 liters, typically 250 mL to 5.5 liters, 250 mL to 5 liters, 250 mL to 4.5 liters, 250 mL to 4 liters, 250 mL to 3.5 liters, 250 mL to 3 liters, 500 mL to 6 liters, 500 mL to 5.5 liters, 500 mL to 5 liters, 500 mL to 4.5 liters, 500 mL to 4 liters, 500 mL to 3.5 liters, 500 mL to 3 liters, more typically 1 liter to 6 liters, 1 liter to 5.5 liters, 1 liter to 5 liters, 1 liter to 4.5 liters, 1 liter to 4 liters, 1 liter to 3.5 liters, even more typically 1 liter to 3 liters, 1.5 liters to 6 liters, 1.5 liters to 5.5 liters, 1.5 liters to 5 liters, 1.5 liters to 4.5 liters, 1.5 liters to 4 liters, 1.5 liters to 3.5 liters, most typically 2 to 3 liters, usually 2.1 to 3 liters. The aqueous neutral to mildly alkaline metal bicarbonate solution may be administered on a full or empty stomach, typically the aqueous neutral to mildly alkaline metal bicarbonate solution is administered on an empty stomach. Usually 1.5 to 3 liters, more typically 1.5 to 2.4 liters, even more typically 1.8 to 2.1 liters and usually between 1.8 and 2.7 liters of aqueous neutral to mildly alkaline metal bicarbonate solution is ingested on an empty stomach in approximately 300 mL volumes at set times each day. The solution may be administered according to these latter dosages over short (for example 1 to 10 days) or long (for example 6 months to 10 years or more) periods as required. Usually the amount of aqueous neutral to mildly alkaline metal bicarbonate solution administered to a mammal is 5 to 100 mL per Kg, more usual 10 to 50 mL per Kg, most usual. 14 to 29 mL per Kg or 25 to 43 mL per Kg.

Typically the aqueous neutral to mildly alkaline metal bicarbonate solution is consumed on an empty stomach. Usually consumption in this manner avoids the mixing of bicarbonate anions with stomach acid which may result in the loss of bicarbonate. Usually the aqueous neutral to mildly alkaline metal bicarbonate solution is consumed in small amounts at set times each day to avoid a rapid increase in the bicarbonate concentration of body fluids. Usually the amount of aqueous neutral to mildly alkaline metal bicarbonate solution consumed at commencement is 500 mL per day and is increased by increments over a period of one month to the maximum consumption. This start-up schedule generally avoids any gastrointestinal side effects due to the smooth muscle relaxation properties of magnesium.

The advantages of the aqueous neutral to mildly alkaline metal bicarbonate solution of the invention are that the magnesium cations function as bicarbonate transporters into body cells. Magnesium bicarbonate enters body cells and the bicarbonate anions function to displace from equilibrium the dissociation reaction of intracellular carbonic acid. Magnesium bicarbonate enters body cells and the bicarbonate anions function as an intracellular proton sink (or proton scavenger). These reactions can be represented by the one equation

$$H_2CO_3 + H_2O \rightleftharpoons H_3O^+ + HCO_3^-$$

Magnesium bicarbonate enters body cells and the bicarbonate anion function to displace from equilibrium the hydration reaction of carbon dioxide which is catalysed by the enzyme carbonic anhydrase. This reaction can be represented by the equation

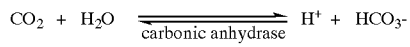

$$CO_2 + H_2O \xrightleftharpoons[]{\text{carbonic anhydrase}} H^+ + HCO_3^-$$

Usually appropriate salts of magnesium, sodium, potassium, calcium and lithium should not exceed the concentrations of the component elements recommended by health authorities. The concentrations of component elements cannot exceed concentrations restricted by the solubility product constants of respective hydroxides and carbonates.

EXAMPLE 1

An Experiment to Decrease Intracellular Proton Concentrations and to Increase Intracellular Bicarbonate Concentrations in Mammalian Cells in vitro Aqueous bicarbonate anions act as proton sinks in the presence of excess proton concentrations in solution. This reaction can be represented by the chemical equation

$$HCO_3^- + H_3O^+ \xrightleftharpoons[]{\text{aqueous}} H_2CO_3 + H_2O$$

In the presence of sufficient concentrations of bicarbonate anions, the reaction is essentially complete and proton concentrations decrease. The pH value of the solution increases. When plasma bicarbonate anions are present outside mammalian body cells in sufficient concentrations, they are translocated into the cytoplasm of the cells across the cell plasma membranes. Indeed, bicarbonate anions equilibrate rapidly across mammalian cell membranes. Bicarbonate translocation into cells takes place via several processes. These processes include a chloride-bicarbonate anion exchange and a sodium dependent chloride-bicarbonate anion exchange and potassium co-transport and magnesium co-transport.

An experiment was conducted to decrease intracellular proton concentrations and to increase intracellular bicarbonate concentrations in mammalian body cells in vitro. Throughout the experiment, extracellular pH determinations were made using a pH electrode and intracellular pH determinations were made using a trapped fluorescein derivative. An increase in intracellular proton concentrations (intracellular acidification) was achieved by applying 10 mmol ammonium chloride ($NH_4Cl$) solution to a suspension of cells and then removing the $NH_4Cl$. An increase in intracellular bicarbonate concentrations was achieved by applying an aqueous metal bicarbonate solution to a suspension of cells. The aqueous metal bicarbonate solution contained approximately $Mg^{2+}$ 120 mg per liter, $Na^+$ 135 mg per liter and $HCO_3^-$ 950 mg per liter at pH 8.3. This aqueous metal bicarbonate solution was equivalent to 15 mmol bicarbonate approximately. Blood was collected in sodium heparin from a range of mammals and the leucocytes removed. The leucocytes were washed and re-suspended in isotonic saline. Intracellular pH determinations were made by loading leucocytes for 15 minutes with (10 micromol in saline) 2,7-bis(carboxyethyl)-5,6-carboxyfluorescein (BCECF). Cells were illuminated at 440 nm and 490 nm and fluorescence was measured at 530 nm.

The experiment utilising sheep leucocytes is given stepwise below:

Step 1. Increase in intracellular proton concentrations (cytoplasmic acidification)

A. Leucocytes suspended in normal saline after pretreatment with fluorescein.

Extracellular pH 7.2

Intracellular pH 7.1

B. 10 mmol ammonium chloride ($NH_4Cl$) solution pH 7.5 applied to suspension of leucocytes for 10 minutes.

C. Leucocytes washed and re-suspended in normal saline.

Extracellular pH 7.3

Intracellular pH 6.1

Result: Cells have increased intracellular proton concentrations. Cytoplasm is acidified.

Step 2. Decrease in intracellular proton concentrations

A. Acidified leucocytes (from Step 1.) divided into two groups; Control group and Treatment group.

B. Treatment group of leucocytes exposed to aqueous metal bicarbonate solution.

After 3 minutes:

Extracellular pH 7.5

Intracellular pH 7.0

C. Control group of leucocytes not exposed to aqueous metal bicarbonate solution.

After 5 minutes:

Extracellular pH 7.2

Intracellular pH 6.6

Result: Cells treated with aqueous metal bicarbonate solution rapidly decrease intracellular proton concentrations. Cytoplasm shows rapid recovery from acidification relative to non-treated cells.

Step 3. Increase in intracellular bicarbonate concentrations

A. Leucocytes suspended in normal saline after pretreatment with fluorescein.

Extracellular pH 7.2

Intracellular pH 7.1

B. Aqueous metal bicarbonate solution applied to suspension of leucocytes for 20 minutes.

Extracellular pH 7.9

Intracellular pH 7.4

Result: Cells treated with aqueous metal bicarbonate solution have increased intracellular bicarbonate concentrations which are manifested by an increase in pH value of cytoplasm.

The experiment was repeated with leucocytes from mice, rats, guinea pigs, cattle, horses, dogs, cats and humans. In all cases, acidified cells treated with aqueous metal bicarbonate solution had decreased intracellular proton concentrations. In all cases, cells treated with aqueous metal bicarbonate solution had increased intracellular bicarbonate concentrations which were manifested by increased pH values of cytoplasm. The experiment was repeated with aqueous metal bicarbonate solutions that contained a range of concentrations of $Mg^{2+}$, $Na^+$, $HCO_3^-$ and $K^+$ and $Ca^{2+}$ ions. Significant results were obtained for the following range of concentrations:

| Ion | Range of concentrations to achieve significant results | | |
|---|---|---|---|
| $Mg^{2+}$ | 20 | to | 120 mg/liter |
| $Na^+$ | 50 | to | 500 mg/liter |
| $K^+$ | 50 | to | 500 mg/liter |
| $Ca^{2+}$ | 20 | to | 150 mg/liter |
| $HCO_3^-$ | 250 | to | 2,100 mg/liter |
| ($HCO_3^-$) | (4 mmol to 35 mmol) | | |

Significant results were obtained for pH range pH 7.5 to 9.5. (pH 9.5 was achieved by the addition of NaOH).

Aqueous metal bicarbonate solutions, containing a range of cation and bicarbonate anion concentrations, decrease intracellular proton concentrations and increase intracellular bicarbonate concentrations in mammalian cells in vitro.

EXAMPLE 2

An Experiment to Demonstrate Bicarbonate Anion Translocation From Aqueous Metal Bicarbonate Solution into the Mammalian Body Against a Bicarbonate Anion Concentration Gradient Mammalian plasma contains bicarbonate anions at a concentration about 25 mmol ($HCO_3^-$ 1,500 mg per liter). When ingested, aqueous metal bicarbonate solution produces biochemical, physiological and medical effects at bicarbonate anion concentrations about 16 mmol ($HCO_3^-$ 950 mg per liter). Aqueous metal bicarbonate solution, at bicarbonate anion concentration about 16 mmol, contains two thirds the bicarbonate anion concentration of plasma, so bicarbonate anions must be translocated into the mammalian body against a bicarbonate anion concentration gradient.

Mammalian plasma contains cations at concentrations around $Mg^{2+}$ 24 mg per liter, $Na^+$ 3,300 mg per liter, $K^+$ 175 mg per liter and $Ca^{2+}$ 100 mg per liter. Aqueous metal bicarbonate solution commonly contains cations at concentrations around $Mg^{2+}$ 120 mg per liter, $Na^+$ 135 mg per liter, $K^+$ 100 mg per liter and $Ca^{2+}$ 20 mg per liter. Aqueous metal bicarbonate solution commonly contains 5 times the magnesium cation concentration of plasma. Other cations are present commonly in aqueous metal bicarbonate solution in concentrations lower than plasma.

The concentrations of cations and anions in plasma can be compared with concentrations of cations and anions in aqueous metal bicarbonate solution by examination of the following table:

| | Concentrations of cations and anions | |
|---|---|---|
| Ion | Plasma | Aqueous metal bicarbonate solution |
| $Cl^-$ | 3,600 mg/liter | 0 mg/liter |
| $Na^+$ | 3,300 mg/liter | 135 mg/liter |
| $HCO_3^-$ | 1,500 mg/liter | 950 mg/liter |
| $K^+$ | 175 mg/liter | 100 mg/liter |

-continued

| | Concentrations of cations and anions | |
|---|---|---|
| Ion | Plasma | Aqueous metal bicarbonate solution |
| $Ca^{2+}$ | 100 mg/liter | 20 mg/liter |
| $Mg^{2+}$ | 24 mg/liter | 120 mg/liter |

It is suggested that sodium cations and chloride anions leave plasma along their respective concentration gradients and magnesium and bicarbonate ions enter plasma along a magnesium cation concentration gradient. Magnesium functions as a bicarbonate transporter. In addition, it is suggested that bicarbonate anions enter plasma by chloride-bicarbonate exchange processes along a chloride anion concentration gradient (chloride 'out', bicarbonate 'in').

In mammals, any large increases in plasma bicarbonate concentrations can be decreased normally by a number of biochemical and physiological homeostatic control processes. These processes occur in time frames that range from minutes to hours and longer. One of the main control processes that occurs as a result of increased plasma bicarbonate concentration is an alteration in bicarbonate chemistry in the kidneys. This is manifested by a decrease in proton concentration in urine and by a pH value of urine that is less acidic. In the presence of increased plasma bicarbonate, kidney tubule cells decrease their excretion of protons. Kidney control of bicarbonate concentration is not instantaneous and occurs within a time frame of several hours to several days. Unless a mammal has physiological or clinical acidosis, it is difficult to detect small increases in plasma bicarbonate concentration. Any increases in plasma bicarbonate concentration are taken up by body cells. Indeed, plasma bicarbonate equilibrates with intracellular bicarbonate rapidly. In a normal mammal, a measurable increase in plasma bicarbonate concentration occurs only during an artificially induced alkalosis and is detectable either when the consumption of bicarbonate anions (as $NaHCO_3$) greatly exceeds the concentration of bicarbonate in normal plasma or when bicarbonate anions (as $NaHCO_3$) are administered intravenously.

An experiment was conducted to determine if bicarbonate anions in aqueous metal bicarbonate solutions are translocated against a bicarbonate concentration gradient into the body. Bicarbonate translocation against a concentration gradient could occur either via energy (ATP) dependent processes or via anion (chloride-bicarbonate) exchange or via co-transport with cations along cation concentration gradients. There are also complex thermodynamic processes involving intracellular and extracellular concentrations of bicarbonate anions, hydroxide anions, protons and carbon dioxide that may assist in the overall translocation of bicarbonate anions. These processes often involve the production of bicarbonate anions by carbonic anhydrase enzymes. In the experiment, entry of bicarbonate anions into the body was assessed by determinations of proton concentration in urine; that is, the pH value of urine.

Ten people had urine pH value assessed once per week for 3 months. Urine pH values were assessed once per week for a further 3 months after commencement of consumption of aqueous metal bicarbonate solution. The aqueous metal bicarbonate solution contained approximately $Mg^{2+}$ 120 mg per liter, $Na^+$ 135 mg per liter and $HCO_3^-$ 950 mg per liter. The major component of the solution was magnesium bicarbonate $Mg(HCO_3)_2$ 720 mg per liter approximately. Results are given below:

| Mean pH value of urine (Early morning sample) | |
|---|---|
| Prior to consumption of aqueous metal bicarbonate solution: | pH 5.9 |
| After commencement of consumption of aqueous metal bicarbonate solution: | pH 6.7 |

The consumption of aqueous metal bicarbonate solution decreases proton excretion by the kidneys. The pH value of urine increases.

These results demonstrate that bicarbonate anions from aqueous metal bicarbonate solution are translocated against a bicarbonate anion concentration gradient into the body. This may occur either via co-transport with cations along a cation concentration gradient or via chloride-bicarbonate exchange processes along a chloride anion concentration gradient (chloride 'out', bicarbonate 'in'). In the case of aqueous metal bicarbonate solution, the only cation concentration gradient possible is that involving magnesium cation concentrations.

The consumption of aqueous metal bicarbonate solution leads to an increase in bicarbonate anion concentration in the body which is manifested by a decrease in proton concentration in urine; an increase in pH value of urine.

EXAMPLE 3

An Experiment to Improve the Buffering Capacities of the Extracellular and Intracellular Bicarbonate Buffers and to Decrease Senescence and to Increase Longevity in a Representative Mammal Mammalian body cells produce continuously concentrations of carbon dioxide. Upon hydration, carbon dioxide increases proton concentrations in the cytoplasm of body cells. The pH values of the cytoplasm of body cells are lowered. The production of protons in cytoplasm by the hydration of carbon dioxide can be represented by the following chemical equations:

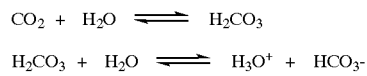

The protons produced in the cytoplasm of body cells by the hydration of carbon dioxide, and other intracellular reactions, are buffered normally by intracellular bicarbonate buffers. The bicarbonate anions in intracellular buffers derive manly from the extracellular bicarbonate of blood plasma. The bicarbonate anions in blood plasma originate from erythrocytes as products of erythrocyte carbonic anhydrase enzyme reactions.

When plasma bicarbonate anions are present outside mammalian body cells in sufficient concentrations, they are translocated into the cytoplasm of the cells across the cell plasma membranes. Indeed, plasma bicarbonate equilibrates with cytoplasmic bicarbonate rapidly. Bicarbonate translocation into cells takes place via several processes. These processes include a chloride-bicarbonate anion exchange and a sodium dependent chloride-bicarbonate anion exchange and potassium co-transport and magnesium co-transport. There are also complex thermodynamic processes involving intracellular and extracellular concentrations of bicarbonate anions, hydroxide ions, protons and carbon dioxide that may assist in the overall translocation of bicarbonate anions. These processes often involve the production of bicarbonate anions by carbonic anhydrase enzymes.

Concentrations of bicarbonate anions that are translocated into mammalian body cells improve the buffering capacity of the cytoplasm of the cells. Concentrations of bicarbonate anions and concentrations of carbon dioxide form a buffer system described by the Henderson-Hasselbalch equation:

$$pH = pK + log([HCO_3^-]/[H_2CO_3])$$

(Where pK is the pK of hydrated carbon dioxide $H_2CO_3$ and has an approximate numerical value of 6.35)

For a classical (closed system) buffer to be effective, the ratio of the conjugate base to the acid (in the above case $[HCO_3^-]/[H_2CO_3]$) must be between 0.1 and 10. This ratio applies also to buffers in biological (open) systems. In mammalian body cells, the continuous and open production of carbon dioxide means that continuous supplies of bicarbonate anions are required to maintain effective and optimal buffering capacities. Under conditions of excess proton concentrations, from carbon dioxide production and ATP hydrolysis and other metabolic processes, the supply of bicarbonate fails and the effective and optimal buffering capacities of mammalian body cells falter.

The vitality of mammalian body cells is linked critically to the buffering capacities of the extracellular fluids and the cytoplasm of the cells. Processes of cellular degeneration occur when buffering capacities falter in the presence of excess proton concentrations. Cellular degenerations are manifested in the mammalian body by degenerative diseases and senescence. Examples of degenerative diseases in mammals that are linked casually to extracellular and intracellular proton concentrations include osteoporosis, osteoarthritis, the diseases associated with chronic inflammation, the diseases associated with lysosomal enzyme activities, the diseases associated with oxidations of cell nucleic acids, cell protein amino acids and cell membrane lipids, and the diseases associated with aberrations of mitochondrial respiration.

An experiment was conducted to improve the buffering capacities of the extracellular and intracellular bicarbonate buffers and to consequently decrease senescence and increase longevity in a representative mammal. One hundred and ten Merino ewe lambs were divided randomly at weaning into a control group and a treatment group. The groups were of equal size and were maintained under similar conditions except for the pH values and aqueous metal bicarbonate concentrations of drinking water supplies. Sheep were selected as the representative mammal because their life span and body weight are more representative of typical mammals than laboratory rodents, their life span is not excessively long, their body size permits multiple blood and tissue sample collections, they are easy to handle and their husbandry is suited to experimental conditions. The control group was maintained, for the full life span of the sheep, in small experimental paddocks with slightly acidic (less than pH 6.5) drinking water supplies that contained bicarbonate concentrations less than 30 mg per liter. The treatment group was maintained, for the full life span of the sheep, in small experimental paddocks with slightly alkaline (pH 7.8 to 9.0) drinking water supplies that contained bicarbonate concentrations between 300 mg per liter and 800 mg per liter. The drinking water supplies for the treatment group were loaded with the appropriate concentrations of bicarbonate anions by the addition of crushed and powdered magnesite $MgCO_3$ to the water. The magnesite frequently contained calcite $CaCO_3$ and dolomite $(Ca,Mg)CO_3$. The magnesite was dissolved in the drinking water either with the assistance of commercial supplies of carbon dioxide gas or carbonic acid or with local supplies of hydrated carbon dioxide. This dissolution process can be represented by the following chemical equations:

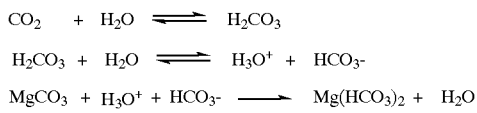

The treatment group of sheep consumed slightly alkaline (pH 7.8 to 9.0) drinking water that contained bicarbonate concentrations between 300 mg per liter and 800 mg per liter. At this pH value, and this bicarbonate concentration, bicarbonate was mostly in the form of magnesium bicarbonate $Mg(HCO_3)_2$:

In addition, some sediments of carbonate $(Ca,Mg)CO_3$ were present in the drinking water during summer months:

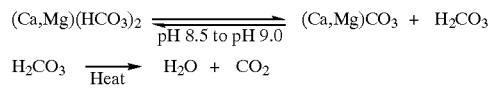

The mean pH values and the mean magnesium, calcium and bicarbonate concentrations in the drinking water supplies are given below (the concentrations of cations and bicarbonate anions were not stoichiometric in the drinking water—particularly the drinking water of the control group—because of the presence of some concentrations of sulphate, chloride and sodium ions):

| Means of parameters in drinking water | | |
|---|---|---|
| | Control Group | Treatment Group |
| pH | 6.1 | 8.4 |
| $Mg^{2+}$ mg/liter | 13 | 110 |
| $Ca^{2+}$ mg/liter | 20 | 30 |
| $HCO_3^-$ mg/liter | 25 | 660 |

In the late stages of pregnancy, there is a tendency for pregnant mammals to become hypoglycaemic and hyperketonaemic. Hyperketonaemia subjects the pregnant mammal to an acid load (increase in proton concentrations). This acid load may result in clinical acidosis. Like all mammals, pregnant ewes tend to be hypoglycaemic and hyperketonaemic late in pregnancy. In ewes affected clinically with acidosis, bicarbonate concentration range between 14 to 20 mmol per liter plasma.

Over several years, plasma bicarbonate concentrations were determined for the control group and the treatment group one week prior to lambing. Determination of plasma bicarbonate concentrations prior to lambing is a direct measure of extracellular and intracellular bicarbonate buffering capacity. In ewes with effective extracellular and intracellular bicarbonate buffers, bicarbonate concentrations are maintained in a range between 24 and 27 mmol per liter plasma. Plasma bicarbonate concentrations are given below:

| Mean plasma bicarbonate concentrations one week prior to lambing (mmol per liter) | | |
|---|---|---|
| Age (years) | Control Group | Treatment Group |
| 4 | 24.9 | 26.1 |
| 6 | 22.8 | 25.9 |
| 8 | 22.2 | 26.4 |
| 10 | 21.9 | 25.8 |

The treatment group had larger plasma bicarbonate concentrations than the control group.

The treatment group had larger plasma bicarbonate concentrations than the control group.

The consumption of aqueous metal bicarbonate solution, principally magensium bicarbonate solution, improves the buffering capacities of extracellular and intracellular bicarbonate buffers in mammals.

In mammalian demography, there are two measurements utilised commonly in the experimental study of degenerative diseases and senescence. The first measurement is called fifty percent survival. Fifty percent survival describes the chronological age at which half an original population has died. The second measurement is called maximum life span. Maximum life span describes the age of the longest lived survivors of a population. The fifty percent survival measurement is considered to reflect susceptibility to accidents and infectious and degenerative diseases in mammals. The maximum life span measurement is is considered to reflect the innate processes of senescence in mammals. The fifty percent survival measurement and the maximum life span measurement for the control group and the treatment group are given below:

| Fifty percent survival | |
|---|---|
| Control group | 8 years |
| Treatment group | 11 years |
| Maximum life span | |
| Control group | 13 years |
| Treatment group | 17 years |

The treatment group had a larger fifty percent survival measurement and a larger maximum life span measurement than the control group.

The death of each member of a population of mammals can be plotted graphically. The continuous function representing mortality in a population is known as a survival curve. Survival curves for the control group and treatment group are represented in FIG. 1.

The survival curves show that more mature sheep were alive in the treatment group than the control group at any time. This occurred with the consumption of normal physiological volumes of water (as aqueous metal bicarbonate solution).

The consumption of aqueous metal bicarbonate solution, extends the maximum life span of mammals by at least twenty percent and increases the number of mature mammals alive at any time.

Senescence in mammals is characterised by progressive oxidations of the structural and function molecules that constitute body cells and tissues. These oxidations occur particularly in nucleic acids, protein amino acids and cell membrane lipids.

Because protons often participate in biological redox reactions, oxidations of many structural and functional molecules in body cells and tissues are increased in rate by the presence of excess proton concentrations. Oxidations of structural and functional molecules are increased in rate by acidic conditions.

In general, oxidations of molecules are linked to proton concentrations described by a formulation of the Gibbs energy equation $$E_{pH} + E_m + 2.3RT/Flog([oxidised]/[reduced])$$

where $E_{pH}$ is a measure of oxidising power at a particular pH value and $E_m$ is the mid-point potential. In practice, $E_{pH}$ is decreased by between −30 mV and −60 mV for each decrease in proton concentration by a factor of 10. That is, oxidising power is decreased by between −30 mV and −60 mV for each increase in pH value by 1 pH unit.

Oxidations of nucleic acids and protein amino acids lead to nucleic acid and protein degradation respectively. These degradations lead to senescence in mammals. Nucleic acid degradation is manifested by either cell death or cell transformation to the cancerous state. Protein degradation is manifested by increased urea concentrations in the body which can be detected in the plasma.

Determination of plasma urea concentrations in elderly mammals is a direct measure of amino acid oxidation, protein degradation and overall nitrogen (anabolic/catabolic) balance. Determination of plasma urea concentrations in elderly mammals is a direct measure of cellular degenerations and senescence.

Over several years, plasma urea concentrations were determined for the control group and the treatment group. Plasma urea concentrations are given below:

| Mean plasma urea concentrations in elderly sheep (mmol per liter) | | |
|---|---|---|
| Age (years) | Control Group | Treatment Group |
| 8 | 11 | 5 |
| 10 | 13 | 3 |
| 12 | 13 | 7 |

The treatment group had smaller plasma urea concentrations than the control group.

The treatment group had smaller plasma urea concentrations than the control group.

The consumption of aqueous metal bicarbonate solution, principally magnesium-bicarbonate solution, decreases amino acid oxidations, decreases protein degradation and improves overall nitrogen (anabolic/catabolic) balance in mammals. The consumption of aqueous metal bicarbonate solution, principally magnesium bicarbonate solution, delays cellular degenerations and senescence in mammals.

Autopsies were performed on sheep, when conditions permitted, within 24 hours of death. Macroscopic signs of significant degenerative diseases and other diseases were recorded. Significant pathology is given below:

| Prevalence of pathology at autopsy (%) | | |
|---|---|---|
| Macroscopic Significant Pathology | Control Group | Treatment Group |
| (*most significant) | (42 autopsies) | (38 autopsies) |
| Lungs | 24% | 21% |
| *Heart | 29% | 11% |
| Liver | 43% | 21% |

-continued

| Prevalence of pathology at autopsy (%) | | |
|---|---|---|
| Macroscopic Significant Pathology | Control Group | Treatment Group |
| Kidney | 24% | 16% |
| Other Genito-urinary | 17% | 16% |
| Lymph nodes | 40% | 37% |
| Intestinal tract | 10% | 8% |
| *Joints | 43% | 5% |
| *Bone | 24% | 3% |
| Teeth | 71% | 40% |
| *Skin-wool | 48% | 21% |
| Cancer | 12% | 3% |

The treatment group had a lower overall prevalence of pathology than the control group. In general, pathology in the treatment group was delayed (sheep were older at autopsy) and progression was less advanced.

The treatment group had a lower overall prevalence of pathology than the control group. In general, pathology in the treatment group was delayed (sheep were older at autopsy) and progression was less advanced.

The consumption of aqueous metal bicarbonate solution, principally magnesium bicarbonate solution, decreases the prevalence of joint pathology (arthritis) and bone pathology (osteoporosis) and cardiac pathology and skin pathology most significantly and decreases the overall prevalence of the pathology of most organs.

EXAMPLE 4

An Experiment to Distinguish Between the Consumption of Magnesium Bicarbonate and the Consumption of Magnesium Cations per se in Increasing Longevity in a Mammal An experiment was conducted to assess if the consumption of magnesium bicarbonate increased longevity in a mammal compared to the consumption of magnesium cations per se. A short-lived mammalian species was chosen. Short-lived mammals possess high. levels of proton leak across inner mitochondrial membranes, high levels of carbonic anhydrase enzyme activities (for acid production) and high levels of spontaneous cancer development and spontaneous death. Any increase in longevity in a short-lived species is indicative of an improvement in fundamental cell biochemistry. Two hundred outbred (Swiss) female mice were divided randomly at weaning into two groups of 100 mice and were maintained under identical management and environmental conditions.

One group of mice was supplied with drinking water that consisted of aqueous metal bicarbonate solution with a pH value between pH 8.1 and pH 8.5. The aqueous metal bicarbonate solution contained approximately $Mg^{2+}$ 120 mg per liter, $Na^+$ 135 mg per liter and $HCO_3^-$ 950mg per liter. The major component of the solution was magnesium bicarbonate $Mg(HCO_3)_2$ 720mg per liter approximately. The second group of mice was supplied with drinking water that contained magnesium sulphate (Epsom salts) 1 gram per liter with a pH value between pH 6.5 and pH 7.0. This drinking water contained approximately $Mg^{2+}$ 120mg per liter. Bicarbonate anions were absent.

Both groups of mice were fed commercial laboratory food that contained 1 gram of magnesium per kilogram of food. Both groups of mice were fed on alternate days with no food available on the other days. Group-specific drinking water (as described above) was available at all times. Feeding on alternate days decreased the possible loss of bicarbonate anions by stomach acid and food ingesta.

Results of the experiment are given below:

| Fifty Percent Survival | |
|---|---|
| Group consuming magnesium bicarbonate | 790 days |
| Group consuming magnesium sulphate | 736 days |
| Maximum Life Span | |
| Group consuming magnesium bicarbonate | 1152 days |
| Group consuming magnesium sulphate | 1040 days |

The group of mice consuming aqueous metal bicarbonate solution had longevity increased by ten percent compared to the group of mice consuming magnesium cations per se.

The group of mice consuming aqueous metal bicarbonate solution had longevity increased by ten percent compared to the group of mice consuming magnesium cation per se.

The consumption of aqueous metal bicarbonate solution, principally magnesium bicarbonate solution, extends the maximum life span of mammals by ten percent more than the consumption of magnesium cations per se.

EXAMPLE 5

An Experiment to Decrease the Clinical Signs of Osteoarthritis

Osteoarthritis is a disease of degeneration. There is degradation and inflammation of the joints of the body. Osteoarthritis is defined as a disease process involving a disturbance of the normal balance of degradation and repair in the articular cartilage and subchondral bone of joints. This disturbance of balance causes areas of morphological damage and results in clinical problems such as pain and disability. Osteoarthritis is manifested as a slowly progressive degeneration of the joints of the hands and large weight-bearing joints (hips and knees). It is common in post menopausal women. Osteoarthritis is characterised by pain, enlargement of joints and limitation of joint movements. The linings of osteoarthritic joints show a moderate to marked degree of inflammation. The principle pathological changes associated with osteoarthritis are destruction of joint cartilage and neoformations of bone at joint margins (osteophytes). In osteoarthritis, destruction of joint cartilage is caused by acid protease enzymes (and other enzymes) derived often from the lysosomes of cartilage cells (chondrocytes), inflammatory cells and other cells.

Acid protease enzymes possess optimal activity in an acidic environment; that is, an environment with high proton concentrations. Proton concentrations involved in the pathogenesis of osteoarthritis derive from the hydration of carbon dioxide catalysed by intracellular carbonic anhydrase enzymes. The production of protons by carbonic anhydrase enzymes can be represented by the equation

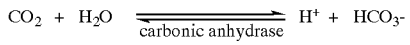

Protons formed by carbonic anhydrase enzymes are concentrated by intracellular V-type proton pumps and stored in the endosomes and lysosomes of body cells.

Functional endosomes and lysosomes maintain internal concentrations of protons which give them internal pH values between pH 3.0 and pH 6.0. Many degenerative diseases, including osteoarthritis, involve intracellular and extracellular release of lysosomal enzymes. In osteoarthritis, chemical fluxes through the reactions catalysed by lysosomal enzymes result in the breakdown of cartilage and bone.

An experiment was conducted to assess if the clinical signs of osteoarthritis could be decreased by the consumption of aqueous metal bicarbonate solution. The clinical signs of osteoarthritis include pain, swelling, inflammation, skin discoloration, joint deformities and decrease in joint function. An increase in extracellular and intracellular bicarbonate anion concentrations would decrease the production of protons from reactions catalysed by carbonic anhydrase enzymes, decrease the pumping of protons by V-type proton pumps, decrease the activities of acid protease enzymes and decrease other activities of lysosomes. The clinical signs of osteoarthritis would be alleviated. A group of ten people were chosen who had been diagnosed with having osteoarthritis. Each person in the group had been suffering from (clinical) osteoarthritis for between 2 and 5 years. Five of the group were post menopausal women who had clinical signs of osteoarthritis in the joints of their hands. The osteoarthritic joints included the distal and proximal interphalangeal joints of the fingers and the carpometacarpal joint of the thumbs. In all 5 cases, loss of joint function was moderate to severe.

Figure 2:
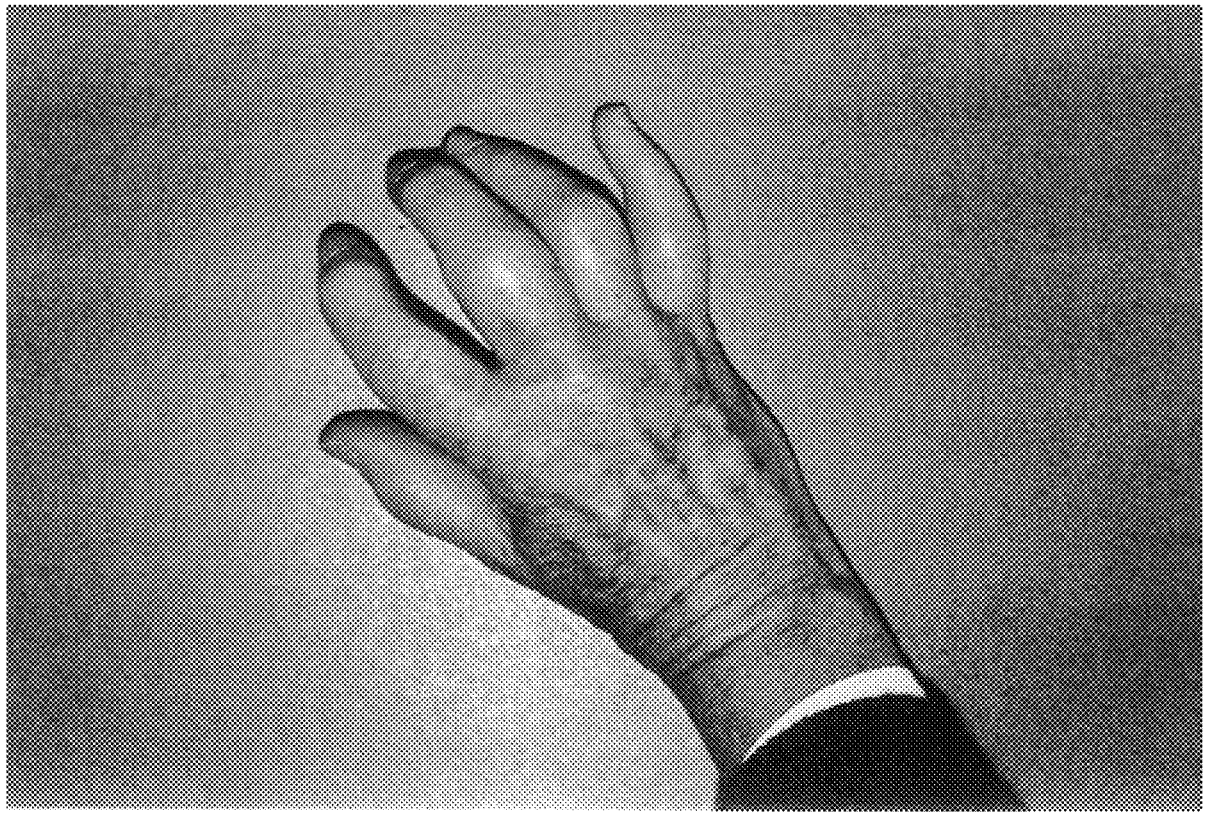
FIG. 2 is a photograph showing osteoarthritis in the joints of the fmgers and thumb. Osteoarthritis before the consumption of aqueous metal bicarbonate solution. Note the swelling and 'claw-like' hand resulting from joint flexion and joint displacement. (The patient was pushing down with her hand 'as hard as possible' in an attempt to place her hand flat on the underlying surface.)

In all 5 cases, the women suffered pain, swelling of the fingers and loss of joint movement. Mucous cysts were associated with distal joint osteoarthritis. Lateral deformities occurred in some proximal joints with severe loss of joint function. Women with affected thumbs had considerable loss of function and considerable pain. Many hands were "claw-like" in appearance (FIG. 2). The remainder of the group had osteoarthritis in the hips and knees. These people suffered pain and moderate loss of joint functions.

The people consumed aqueous metal bicarbonate solution with a pH value between pH 8.1 and 8.5. The aqueous metal bicarbonate solution contained approximately $Mg^{2+}$ 120 mg per liter, $Na^+$ 135 mg per liter and $HCO_3^-$ 950 mg per liter. The major component of the solution was magnesium bicarbonate $Mg(HCO_3)_2$ 720 mg per liter approximately.

Consumption of the aqueous metal bicarbonate solution was commenced at half a liter per day and increased by increments over a period of one month to between 2 to 3 liters per day. Consumption occurred on an empty stomach to avoid the loss of bicarbonate by stomach acid (HCl). Consumption occurred in small amounts (300 ml) at set times each day to avoid rapid increases in bicarbonate concentrations of body fluids and to avoid over hydration.

The results of the experiment were unequivocal. Within 3 to 6 months, all participants in the experiment demonstrated substantial decreases in the clinical signs of osteoarthritis.

Figure 3:
FIG. 3 is a photograph showing osteoarthritis in the joints of the fingers and thumb. Osteoarthritis twelve months after commencement of the consumption of aqueous metal bicarbonate solution. Note that the fingers can be extended and the joints are 'straighter' than twelve months previously. (The patient had placed her hand flat on the underlying surface without exerting any force.)

In all cases, there were remissions in the clinical signs of osteoarthritis which were quantifiable by standard tests of movement, flexibility and strength. The participants showed considerable increases in joint functions and decreases in acute and chronic joint swellings. The "stabbing" pain of osteoarthritis was alleviated. Some participants had remissions of inflammation and arthritis to the stage where many chronic swellings were no longer observable and joint mobilities and functions were restored (FIG. 3).

People in the experiment consumed aqueous metal bicarbonate solution continuously for at least 2 years. During this period, there was evidence of progressive improvement in healing processes. Mucous cysts associated with distal joint osteoarthritis were no longer visible.

Remissions in the clinical signs of osteoarthritis were maintained only with the continual consumption of aqueous metal bicarbonate solution. Once the consumption of aqueous metal bicarbonate solution was halted, clinical signs of pain and swelling began to reappear within 10 days. Clinical signs again went into remission upon continuation of consumption of aqueous metal bicarbonate solution.

The consumption of aqueous metal bicarbonate solution, principally magnesium bicarbonate solution, results in remissions in the clinical signs of osteoarthritis.

Example 6

An Experiment to Maintain and Improve Motor Activity in Mammals. An Experiment to Decrease Fatigue and Lethargy and Improve Motor Activity. An Experiment to Decrease the Fatigue and Lethargy of Chronic Disease and Improve Motor Activity Mammals convert food energy into chemical energy that can be used by body cells to maintain essential cell processes and cell functions. The main chemical energy in mammalian body cells is the chemical ATP (adenosine triphosphate). ATP is synthesised mainly in the mitochondria of body cells. Mitochondrial ATP production is linked intimately to the respiration rates of mitochondria. The respiration rates of mitochondria are dependent on many factors including the proton concentrations (pH values) of the cytoplasm of body cells. If the intracellular bicarbonate buffer of mammalian body cells is not maintained, and is not finctional, proton concentrations increase in the cytoplasm and the pH value of the cytoplasm decreases. When proton concentrations increase in the cytoplasm sufficiently (pH value decreases sufficiently) the respiration rates of mitochondria are diminished. When the respiration rates of mitochondria are diminished, the production of ATP is diminished. When the production of ATP is diminished, ATP concentrations in the cell decrease and the main chemical energy source for mammalian body cells becomes depleted. Under these conditions, body cells cannot maintain essential cell processes and cell functions. The body becomes fatigued and lethargic.

In addition to the hydration of carbon dioxide per se, one of the sources of increased proton concentrations in the cytoplasm of body cells is the hydrolysis of ATP. The hydrolysis of ATP can be represented by the chemical equation

$$ATP + H_2O \rightleftharpoons ADP + P_i + H^+$$

Increased proton concentrations from the hydrolysis of ATP occur particularly in the cytoplasm of muscle cells during muscular (motor) activity. This is referred to often as an increase in 'lactic acid' (the lactic acid is, in fact, lactate derived from glycolysis and the 'acid' is the protons derived from ATP hydrolysis).

An experiment was conducted to assess if motor activity could be maintained and improved in mammals by improving the buffering capacity of the extracellular and intracellular bicarbonate buffers.

Two hundred inbred (Balb c) female mice were divided randomly at weaning into two groups of 100 mice and maintained under identical conditions for 3 years. Control groups of mice were given drinking water that was deionised and slightly acidic (pH 5.0). Treatment groups of mice were given drinking water that consisted of aqueous metal bicarbonate solution with a pH value between pH 8.1 and 8.5. The aqueous metal bicarbonate solution contained approximately $Mg^{2+}$ 120 mg per liter, $Na^+$ 135 mg per liter and $HCO_3^-$ 950 mg per liter. The major component of the solution was magnesium bicarbonate $Mg(HCO_3)_2$ 720 mg per liter approximately.

Motor activity in mice was assessed at regular intervals for a 12 month period between 1 year and 2 years of age. Results of the experiment are given below:

| Mean motor activity in mice | | |
|---|---|---|
| | Control Group | Treatment Group |
| Mean number of mice per hour climbing to lid of cage | 26 | 95 |
| Mean number of mice per hour engaged in exploratory activity | 48 | 82 |
| Mean time to exhaustion during enforced motor activity | 5 minutes | 9 minutes |

The treatment group had improved motor activity relative to the control group.

The treatment group had improved motor activity relative to the control group.

The consumption of aqueous metal bicarbonate solution, principally magnesium bicarbonate solution, maintains and improves motor activity in mammals.

Mitochondria are described as 'efficient' if they maintain sufficient production of ATP for maintenance of essential cell processes and cell functions. Efficient mitochondria are the mitochondria of young mammals.

In mammals, there are declines in the efficiencies of mitochondria which are correlated to chronological age. The capacities of cells to maintain their particular energy requirements are diminished progressively with chronological age. Cells that are unable to meet their particular energy requirements undergo senescence, become non-functional and decline progressively towards cell death. This is manifested by body senescence and ageing.

Mitochondria are described as 'inefficient' if they cannot maintain the necessary production of ATP for maintenance of essential cell processes and cell functions. Mitochondrial inefficiency arises from oxidative damage to mitochondrial nucleic acids, mitochondrial enzymes and mitochondrial membrane proteins and lipids. Inefficient mitochondria gradually and progressively dominate in body cells through middle age to old age. Middle aged and elderly mammals are fatigued and lethargic relative to the young. Normal body cells attempt to produce buffers that maintain a cytoplasmic pH value of about pH 7.2. In vitro, if mitochondria are placed for a period in a medium either with an improved buffer at pH 7.2 or with a pH value buffered slightly higher than pH 7.2, there occurs an increase in mitochondrial respiration rate and an increase in the production of ATP.

An experiment was conducted to assess if fatigue and lethargy could be decreased and motor activity improved by improving the buffering capacity of the cytoplasmic bicarbonate buffer in a group of middle aged and elderly people.

Improving the buffering capacity of the cytoplasmic bicarbonate buffer would increase mitochondrial respiration rate and increase the production of ATP. Mitochondria would become more 'efficient'. More chemical energy would be available for maintenance of essential cell processes and cell functions. Fatigue and lethargy would decrease and motor activity would improve.

A group of nineteen people were chosen, with a mean age of 61 years, who had a history of fatigue and lethargy. In the context of this experiment, fatigue and lethargy were determined as subjective feelings of general exhaustion which were manifested by mild to moderate lack of function. The people consumed aqueous metal bicarbonate solution with a pH value between pH 8.1 and 8.5. The aqueous metal bicarbonate solution contained approximately $Mg^{2+}$ 120 mg per liter, $Na^+$ 135 mg per liter and $HCO_3^-$ 950 mg per liter. The major component of the solution was magnesium bicarbonate $Mg(HCO_3)_2$ 720 mg per liter approximately.

Consumption of the aqueous metal bicarbonate solution was commenced at half a liter per day and increased by increments over a period of one month to between 2 to 3 liters per day. Consumption occurred on an empty stomach to avoid the loss of bicarbonate by stomach acid (HCl). Consumption occurred in small amounts (300 ml) at set times each day to avoid rapid increases in bicarbonate concentrations of body fluids and to avoid over hydration.

The results of the experiment were unequivocal. Within 3 months, all participants in the experiment demonstrated substantial decreases in fatigue and lethargy. All participants described a feeling of well-being (mild euphoria). All participants demonstrated an increased capacity for mild physical activity; an improvement in motor activity. Function was restored.

The consumption of aqueous metal bicarbonate solution, principally magnesium bicarbonate solution, decreases fatigue and lethargy and improves motor activity in middle aged and elderly people.

Chronic disease (including degenerative disease) is manifested often by chronic fatigue and lethargy and chronic pain. This is true particularly for chronic inflammatory diseases and autoimmune diseases.

The fatigue, lethargy and pain of chronic disease are correlated often to the high proton concentrations involved in the pathogenesis of chronic disease. In addition to the hydration of carbon dioxide per se, proton concentrations involved in the pathogenesis of chronic disease derive from the hydration of carbon dioxide catalysed by intracellular carbonic anhydrase enzymes. The production of protons by carbonic anhydrase enzymes can be represented by the equation

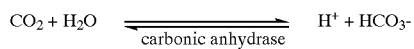

$$CO_2 + H_2O \xrightleftharpoons[\text{carbonic anhydrase}]{} H^+ + HCO_3^-$$

Protons formed by carbonic anhydrase enzymes are concentrated often by V-type proton pumps and stored in endosomes and lysosomes in the cell. The breakdown of endosomes and lysosomes creates concentrations of protons in the cell cytoplasm. This lowers the pH value of the cytoplasm and decreases the production of ATP in mitochondria. Cells become energy deficient. Cells are unable to maintain essential cell processes and cell functions. the body becomes fatigued and lethargic.

Functional endosomes and lysosomes maintain internal concentrations of protons which give them internal pH values between pH 3.0 and pH 6.0. Many of the chronic and degenerative diseases of the body involve intracellular lysosomal activities and intracellular and extracellular release of lysosomal enzymes. Chemical fluxes through the reactions catalysed by lysosomal enzymes result in the breakdown of cells and tissues. Many lysosomal enzymes require low pH values for optimal activity. Some of these enzymes are known as acid protease enzymes.

Lysosomes located in cells known as macrophages, and in some other cells, are involved in antigen processing and antigen presentation. Antigen processing and presentation leads to cell to cell interactions within the immune system which triggers release of a set of chemicals called cytokines. Cytokine concentrations in the body are correlated often to many of the clinical signs of inflammation and disease. These clinical signs include heat, swelling, pain, fatigue and lethargy.

An experiment was conducted to assess if fatigue and lethargy could be decreased and motor activity improved by improving the buffering capacity of the cytoplasmic bicarbonate buffer in a group of people diagnosed and suffering with chronic disease.

Improving the buffering capacity of the cytoplasmic bicarbonic buffer would decrease the hydration of carbon dioxide per se, would decrease the production of protons from reactions catalysed by carbonic anhydrase enzymes, decrease the pumping of protons by V-type proton pumps, decrease the activities of acid protease enzymes, decrease the activities of lysosomes, decrease antigen processing and presentation, and increase the production of ATP. Fatigue and lethargy would decrease and motor activity would improve. Some of the clinical signs of chronic disease would be alleviated.

A group of twenty three people were chosen who had been diagnosed with having chronic disease. Each person had been suffering from chronic disease for between 3 and 8 years. The diseases consisted of chronic viral diseases, chronic inflammatory diseases and autoimmune diseases and included rheumatoid arthritis and dermatitis. All people had a history of fatigue and lethargy. In the context of this experiment, fatigue and lethargy were determined as subjective feelings of general exhaustion which were manifested by moderate to severe lack of function. The people consumed aqueous metal bicarbonate solution with a pH value between pH 8.1 and 8.5. The aqueous metal bicarbonate solution contained approximately $Mg^{2+}$ 120 mg per liter, $Na^+$ 135 mg per liter, $K^+$ 100 mg per liter and $HCO_3^-$ 1,100 mg per liter. The major component of the solution was magnesium bicarbonate $Mg(HCO_3)_2$ 720 mg per liter approximately. Potassium bicarbonate 250 mg per liter was a component of the aqueous metal bicarbonate solution to improve the co-transport of bicarbonate anions into body cells. Consumption of the aqueous metal bicarbonate solution was commenced at half a liter per day and increased by increments over a period of one month to between 2 to 3 liters per day. Consumption occurred on an empty stomach to avoid the loss of bicarbonate by stomach acid (HCl). Consumption occurred in small amounts (300 ml) at set times each day to avoid rapid increases in bicarbonate concentrations of body fluids and to avoid over hydration.

The results of the experiment were delayed but unequivocal. Within 3 to 9 months, all participants in the experiment demonstrated substantial decreases in fatigue and lethargy. All participants demonstrated an increased capacity for mild physical activity; an improvement in motor activity. Function was improved. Those participants with chronic rheumatoid disease (rheumatoid arthritis) demonstrated some decreases in inflammation and some decreases in pain. Those participants with chronic skin disease (dermatitis) demonstrated decreases in inflammation. Those participants with tissue calcification demonstrated decreases in calcium deposits.

The consumption of aqueous metal bicarbonate solution, principally magnesium bicarbonate solution, decreases fatigue and lethargy and improves motor activity in people suffering with chronic disease.

The consumption of aqueous metal bicarbonate solution, principally magnesium bicarbonate solution, decreases clinical signs of inflammation and pain and calcification in people suffering with chronic disease.

Example 7

An Experiment to Prevent and to Treat the Clinical Signs of Diseases Caused by Viruses that Require Proton Concentrations for Infectivity Many viruses become infective by utilising high intracellular proton concentrations in host cells. Proton concentrations involved in the infectivity of viruses, and the pathogenesis of viral diseases, derive from the hydration of carbon dioxide catalysed by intracellular carbonic anhydrase enzymes. The production of protons by carbonic anhydrase enzymes can be represented by the equation $$CO_2 + H_2O \underset{\text{carbonic anhydrase}}{\rightleftharpoons} H^+ + HCO_3^-$$

Protons formed by carbonic anhydrase enzymes are concentrated by intracellular V-type proton pumps and stored in the endosomes and lysosomes of body cells. Functional endosomes and lysosomes maintain internal concentrations of protons which give them internal pH values between pH 3.0 and pH 6.0.

Virus infectivity often requires the activities of acid protease enzymes. Acid protease enzymes are enzymes that function optimally at acidic pH levels. Acid protease enzymes are located in endosomes and lysosomes of body cells.

Influenza viruses require acid protease enzyme activities for their replication and infectivity. The acid proteases of lysosomes and endosomes in body cells act to liberate the nucleic acid (RNA) of the influenza virus from the outer viral membrane.

Many viruses contain their own acid-dependent enzymes which utilise proton concentrations in host cells. For example, the acid proteases of lentiviruses are required for virus protein assembly and viral infectivity.

An experiment was instigated with the aim of preventing and treating the clinical signs of diseases caused by viruses that require proton concentrations for infectivity. Natural infections with influenza viruses and flu-like respiratory viruses were taken as the model infections. Influenza is an acute febrile infectious respiratory disease manifested by inflammation of the bronchial mucosa. It is complicated often by bacterial pneumonia. Clinical signs of influenza include initially fever, malaise, headache and muscle pain followed by coughing, sneezing and respiratory tract effusions. Flu-like respiratory viruses cause respiratory diseases manifested generally by clinical signs of less intensity. than influenza.

Twenty people were chosen and divided into two equal groups. The control group did not consume aqueous metal bicarbonate solution. The treatment group consumed aqueous metal bicarbonate solution with a pH value between 8.1 and 8.5. The aqueous metal bicarbonate solution contained approximately $Mg^{2+}$ 120 mg per liter, $Na^+$ 135 mg per liter and $HCO_3^-$ 950 mg per liter. The major component of the solution was magnesium bicarbonate $Mg(HCO_3)_2$ 720 mg per liter approximately. Consumption of the aqueous metal bicarbonate solution was commenced at half a liter per day and increased by increments over a period of one month to between 2 to 3 liters per day. Consumption occurred on an empty stomach to avoid the loss of bicarbonate by stomach acid (HCl). Consumption occurred in small amounts (300 ml) at set times each day to avoid rapid increases in bicarbonate concentrations of body fluids and to avoid over hydration.

Aqueous metal bicarbonate solution was consumed by people in the treatment group for 2 years.

People in both groups worked either in child care centres or in homes for the elderly and were exposed to influenza and other respiratory infections over a 2 year period. Clinical signs of influenza and flu-like virus infections were observed and recorded over the 2 years. Results are given below:

Record of influenza and flu-like virus infections over a 2 year period

|  | Control Group | Treatment Group |
|---|---|---|
| Influenza |  |  |
| Number of infections | 8 | 2 |
| Duration of symptoms | 5 to 10 days | 2 to 3 days |
| Severity of symptoms (0 to 4) | 4 | 1 to 2 |
| Flu-like viruses |  |  |
| Number of infections | 15 | 3 |
| Duration of symptoms | 3 to 7 days | 2 to 3 days |
| Severity of symptoms (0 to 4) | 2 to 4 | 1 to 2 |

People consuming aqueous metal bicarbonate solution had a lower prevalence of the clinical signs of influenza and flu-like virus infections than people not consuming aqueous metal bicarbonate solution. People consuming aqueous metal bicarbonate solution had less severe symptoms and shorter duration of symptoms than people not consuming aqueous metal bicarbonate solution.

The consumption of aqueous metal bicarbonate solution, principally magnesium bicarbonate solution, decreases the prevalence of the clinical signs of diseases caused by viruses that require proton concentrations for infectivity.

The consumption of aqueous metal bicarbonate solution, principally magnesium bicarbonate solution, decreases the severity and the duration of the clinical signs of diseases caused by viruses that require proton concentrations for infectivity.

EXAMPLE 8

Suitable Formulation and Range of Parameters and Range of Administration Volumes for the Aqueous Metal Bicarbonate Solution A suitable formulation for the aqueous metal bicarbonate solution contains $Mg(HCO_3)_2$ 720 mg per liter approximately ($Mg^{2+}$ 120 mg per liter and $HCO_3^-$ 600 mg per liter approximately). The formulation usually contains also $NaHCO_3$ 485 mg per liter approximately ($Na^+$ 135 mg per liter and $HCO_3^-$ 350 mg per liter approximately). The pH of the formulation is pH 8.3. The formulation is stored either at 5° C. to 10° C. at 1 atmosphere in a sealed container or at higher temperatures at higher pressures. The formulation is administered or consumed by a mammalian (typically human) user in 300 ml doses approximately 6 to 10 times per day usually on an empty stomach at approximately equal time intervals throughout the day. Usually the total amount of formulation usually administered is 1.8 to 3 liters per day.

The parameters of a suitable formulation for the aqueous metal bicarbonate solution may be conveniently represented as follows:

| Typical parameter range | Specific parameters |
|---|---|
| $Mg(HCO_3)_2$ 150 mg/liter to saturation solubility per liter | $Mg(HCO_3)_2$ 720 mg/liter ($Mg^{2+}$ 120 mg/liter and $HCO_3^-$ 600 mg/liter) |
| $NaHCO_3$ 0 to 1,000 mg/liter | $NaHCO_3$ 485 mg/liter ($Na^+$ 135 mg/liter and $HCO_3^-$ 350 mg/liter |
| pH 8.0 to 8.5 | pH 8.3 |
| 0° C. to 10° C. at 1 atmosphere | 5° C. to 10° C. at 1 atmosphere |
| 300 ml dose approximately 1 to 15 times per day | 300 ml dose approximately 6 to 10 times per day |

There exists a range of combinations and concentrations of metal cations that may be included in the suitable formulation of the aqueous metal bicarbonate solution. There exists a range of anions (other than bicarbonate) that may be included in stoichiometric amounts with metal cations in the suitable formulation of the aqueous metal bicarbonate solution. There exists a range of concentrations of bicarbonate anions that may be included in stoichiometric amounts with metal cations in the suitable formulation of the aqueous metal bicarbonate solution.

A typical range of parameters that may be combined and included in the suitable formulation of the aqueous metal bicarbonate solution may be conveniently represented as follows:

Final Concentration in Solution

|  | Typical parameter range | Specific parameters |
|---|---|---|
| $Mg^{2+}$ | 50 to 500 mg/liter | 120 to 300 mg/liter |
| $Na^+$ | 50 to 1,000 mg/liter | 120 to 300 mg/liter |
| $K^+$ | 50 to 500 mg/liter | 120 to 300 mg/liter |
| $Ca^{2+}$ | 50 to 500 mg/liter | 120 to 300 mg/liter |
| $HCO_3^-$ | 200 to 3,000 mg/liter | 600 to 2,000 mg/liter |
| Anions other than $HCO_3^-$ (eg. $Cl^-$, $SO_4^{2-}$) | Stoichiometric with metal cation concentrations | |

There exists a range of pH values for the suitable formulation of aqueous metal bicarbonate solution (that includes cation and anion parameter ranges above). The pH values may be conveniently represented as follows:

| Typical pH range | Specific pH range |
|---|---|
| pH 7.5 to 8.8 | pH 8.0 to 8.5 |

Above pH 8.5, the solution tends to become cloudy due to the formulation of metal carbonates ($CO_3^{2-}$).

There exists a range of physical parameters for the suitable formulation of aqueous metal bicarbonate solution (that includes cation and anion parameter ranges above). The physical parameters may be conveniently represented as follows:

| Typical parameter range | Specific parameter range |
| --- | --- |
| 0° C. to 30° C. | 5° C. to 10° C. |
| 1 to 3 atmospheres | 1 atmosphere |

Above 10° C., carbon dioxide leaves solution and the solution tends to become cloudy (with time) due to the formation of metal carbonates ($CO_3^{2-}$). This may be controlled by increasing the pressure on the solution.

There exists a range of volumes of administration for the suitable formulation of metal bicarbonate solution (that includes cation and anion parameter ranges above). The volume of aqueous metal bicarbonate solution administered depends on the purpose for the administration.

The administered volumes of aqueous metal bicarbonate solution may be conveniently represented as follows:

| Purpose for administration of aqueous metal bicarbonate solution | Typical volume range administered to 70 kg human |
| --- | --- |
| Increased longevity and delay in senescence | 1 to 2 liters per day (normal physiological volume requirement for water intake) |
| Prevention of degenerative diseases | 1 to 2 liters per day (normal physiological volume requirement for water intake) |
| Treatment of osteoarthritis | 1.8 to 3.0 liters per day |
| Treatment of chronic disease | 1.8 to 3.0 liters per day |
| Maintain and improve motor activity | 1.8 to 3.0 liters per day |
| Decrease fatigue and lethargy | 1.8 to 3.0 liters per day |
| Prevention and treatment of influenza and other acid-dependent viral diseases | 1.8 to 3.0 liters per day |

Aqueous metal bicarbonate solution is administered typically in 300 ml doses approximately 6 to 10 times per day at equal time intervals throughout the day.

Typically, the solution is allowed to stand prior to consumption until the solution reaches 15° C. to 20° C. (cool room temperature).

A suitable formulation for the aqueous metal bicarbonate solution contains $Mg(HCO_3)_2$ 720 mg per liter at pH 8.3. The formulation usually contains also $NaHCO_3$ 485 mg per liter. The aqueous metal bicarbonate solution may contain a range of cations and anions within a pH range pH 7.5 to 8.8. The aqueous metal bicarbonate solution is administered in volumes ranging from 1 to 3 liters per day.

EXAMPLE 9

Osteoarthritis is a Slowly Progressive degeneration of the joints of the hands and large weight-bearing joints (hips and knees). Osteoarthritis is common in post menopausal women. Osteoarthritis is characterised by pain, enlargement of joints and limitation of joint movements. The linings of osteoarthritic joints show a moderate to marked degree of inflammation. The principle pathological changes associated with osteoarthritis are destruction of joint cartilage and neoformations of bone at joint margins (osteophytes). In osteoarthritis, destruction of joint cartilage is caused by acid protease enzymes (and other enzymes) derived often from the lysosomes of cartilage cells (chondrocytes), inflammatory cells and other cells.

For an experimental trial, a group of post menopausal women were chosen who had clinical signs of osteoarthritis in the joints of their hands. The osteoarthritic joints included the distal and proximal interphalangeal joints of the fingers and the carpometacarpal joint of the thumbs. In all cases, loss of joint function was moderate to severe.

In all cases, the women suffered pain, swelling of the fingers and loss of joint movement. Mucous cysts were associated with distal joint osteoarthritis. Lateral deformities occurred in some proximal joints with severe loss of joint function. Women with affected thumbs had considerable loss of function and considerable pain. Many hands were "claw-like" in appearance. Women consumed magnesium bicarbonate solution, with added sodium bicarbonate. The women consumed between 2 to 3 liters of bicarbonate solution per day. In this solution, the magnesium concentration was approximately 120 mg per liter, sodium concentration was approximately 135 mg per liter and bicarbonate concentration was approximately 950 mg per liter. Consumption was commenced at half a liter per day and increased by increments over a period of one month to 2 to 3 liters per day. Consumption occurred on an empty stomach to avoid the loss of bicarbonate by stomach acid. Consumption occurred in small amounts (300 mL) at set times each day to avoid rapid increases in bicarbonate concentrations of body fluids.

In all cases, there were remissions in the clinical signs of osteoarthritis which were quantifiable by standard tests of movement, flexibility and strength. The participants showed considerable increases in joint functions and decreases in acute and chronic joint swellings. The "stabbing" pain of osteoarthritis was alleviated. Some participants had remissions of inflammation and arthritis to the stage where many chronic swellings were no longer observable and joint mobilities and functions were restored. However, these improvements were maintained only with the continued consumption of bicarbonate anions. Once the consumption of bicarbonate anions ceased, clinical signs of inflammation began to reappear often within a week.

The participants commented on an absence of lethargy and the presence of a feeling of well-being. Magnesium bicarbonate alleviated the pain and swelling associated with osteoarthritis.

None of the participants demonstrated any clinical signs of influenza or other respiratory viral infections over the two year period of the trial. This occurred despite several of the participants working in situations where exposure to viral infections was high (nursing homes and child care centres).

EXAMPLE 10

Influenza is an acute febrile infectious respiratory disease manifested by inflammation of the bronchial mucosa. Influenza is complicated often by bacterial pneumonia which may be fatal.

For an experimental trial, a group of men and women were chosen who worked in situations where exposure to the influenza virus was likely to occur (nursing homes and child care centres). Each person in the experimental group consumed magnesium bicarbonate solution, with added sodium bicarbonate. Each person consumed between 2 to 3 liters of bicarbonate solution per day. In this solution, the magnesium concentration was approximately 120 mg per liter, sodium concentration was approximately 135 mg per liter and bicarbonate concentration was approximately 950 mg per liter.

Consumption was commenced at half a liter per day and increased by increments over a period of one month to 2 to 3 liters per day. Consumption occurred on an empty stomach to avoid the loss of bicarbonate by stomach acid. Consumption occurred in small amounts (300 mL) at set times each day to avoid rapid increases in bicarbonate concentrations of body fluids.

Over the two year period of the experimental trial, no person in the experimental group showed any clinical signs of influenza.

EXAMPLE 11

A suitable formulation for the aqueous metal bicarbonate solution contains 720 mg $Mg(HCO_3)_2$ per liter (120 mg $Mg^{2+}$ per liter and 600 mg $HCO_3^-$ per liter approximately) and 485 mg $NaHCO_3$ per liter (135 mg $Na^+$ per liter and 350 mg $HCO_3^-$ per liter approximately). The pH of this formulation is pH 8.3. This formulation is stored at 5 to 10° C. at 1 atmosphere or it can be stored at higher temperatures at higher pressures. This formulation is administered in 300 mL doses approximately 6 to 10 times per day. That is the amount of formulation usually administered per day is 1.8 to 3 liters per day. The parameters of the formulation may be conveniently represented as follows:

| Typical Parameter Range | Specific Parameters |
|---|---|
| 100 mg - saturation solubility $Mg(HCO_3)_2$ per liter | 720 mg $Mg(HCO_3)_2$ per liter (120 mg $Mg^{2+}$ and 600 mg $HCO_3^-$ per liter) |
| 0–1000 mg $NaHCO_3$ per liter | 485 mg $NaHCO_3$ per liter (135 mg $Na^+$ and 350 mg $HCO_3^-$ per liter) |
| pH 8–8.6, typically 8–8.5 | pH 8.3 |
| 0–10° C. @ 1 atmosphere | 5–10° C. @ 1 atmosphere |
| 300 mL dose approximately 1 to 20 times per day | 300 mL dose approximately 6 to 10 times per day |

EXAMPLE 12

Mitochondria are inefficient if they cannot maintain the necessary production of ATP for maintenance of essential cell processes and cell functions. This inefficiency is due often to functional damage to the mitochondrial inner membrane and other mitochondrial molecules. Inefficient mitochondria are not able to maintain normal carbon, electron and proton fluxes.

However, in middle age, carbon and electron fluxes may be maintained by the synthesis of fatty acids in the cytoplasm of body cells. In body cells of the middle aged, fatty acids can be regarded as carbon and electron sinks necessary for the maintenance of essential fluxes; that is, for the maintenance of essential life processes. The synthesis of fatty acids utilises ATP. However, the fluxes for production of ATP in mitochondria are decreased in middle age. There is a consequent 'energy' deficit. The middle aged are flat and lethargic relative to the young, though they can be regarded as fat by necessity; the necessity of staying alive. In addition to utilisation of cell ATP, the synthesis of fatty acids in body cells adds to the carbon dioxide load of the cells and adds to concentrations of intracellular protons. This occurs because the series of chemical reactions that synthesise fatty acids results in a net utilisation of bicarbonate anions and a net production of carbon dioxide and protons. For example, each molecule of the fatty acid palmitate that is synthesised by cells utilises seven molecules of ATP and seven bicarbonate anions and produces seven molecules of carbon dioxide and seven protons. Of course, fatty acids are oxidised continuously from fat stores in the body which produces even more carbon dioxide. When excess calories are consumed at any chronological age (and converted to fatty acids) the overall carbon dioxide load is considerable. Caloric restricted rodents avoid this extra carbon dioxide load and, as a consequence, they live longer lives with delays in the onset of degenerative diseases.

A trial involving people consuming bicarbonate anions in water was conducted. These people were middle aged and overweight and complained of tiredness and lethargy. No control group was maintained for the duration of the trial (people in an initial control group were unable to consume the volumes of soft water required). People involved in the trial were given a series of lectures on the biochemistry of mitochondrial processes. They were requested to decrease their food (calorie) intake considerably and to avoid dietary fats. Excessive aerobic exercise was not recommended due to the consequent increase in hunger it produces, the large increase in carbon dioxide concentrations that occur with increased aerobic muscle activity and the damage excess activity does to inefficient mitochondria. Indeed, active muscle cells contain nitochondria with most nucleic acid damage relative to other body cells.

The trial consisted of each person consuming between two to three liters per day of a mixture of magnesium bicarbonate and sodium bicarbonate in water. Bicarbonate concentration was established at a maximum of one gram per liter. (This concentration of bicarbonate is well within the concentrations in several water sources utilised for human consumption in Europe. In these waters however, the bicarbonate is in the form of calcium and sodium bicarbonate and pH values often are not very alkaline.) Consumption was commenced at half a liter per day and increased by increments over a period of one month to the maximum consumption. This start-up schedule avoided any gastrointestinal side effects due to the smooth muscle relaxation properties of magnesium. Capillary dilation in the face was apparent in several people (which was interpreted by those affected as rosy, healthy cheeks). The capillary dilation may have been due to magnesium or may have been due to a decrease in activity of renin which is an acid protease enzyme from the kidney that is central to the control of blood pressure. (Renin exerts its effects ultimately by constriction of small blood vessels.)

Each participant in the trial was advised to consume the bicarbonate solution 'on an empty stomach'. Consumption in this manner avoided the mixing of bicarbonate anions with stomach acid which would have resulted in the loss of bicarbonate. Advice was given also to consume the solution in small amounts at set times each day. Consumption in this manner avoided a rapid increase in the bicarbonate concentrations of body fluids.

The results were unequivocal. Body weight was lost at about one half of a kilogram per week after the initial start-up period was completed. Other beneficial effects (more important than weight loss to the participants in the trial) included the absence of lethargy, the presence of a feeling of well-being (mild euphoria) and the increased capacity for mild physical activity. The participants all commented that their 'energy levels' had improved and that their outlook on life had consequently become more positive.

EXAMPLE 13

A heart muscle cell contains mitochondria that occupy one quarter of the cell volume. It is natural to expect the heart to be rich in mitochondria when one considers the workload of the heart and its subsequent requirement for 'energy'. The consumption of magnesium bicarbonate may assist in maintaining efficient mitochondria in heart muscle cells. In the presence of bicarbonate anions, mitochondrial efficiency in heart muscle cells is maintained by processes which include decreases in proton leaks across inner mitochondrial membranes, establishment of proton circuits independent of proton leaks and maintenance of alkaline pH values in mitochondrial matrixes. In the presence of bicarbonate anions, mitochondrial damage and mitochondrial failure are decreased. Efficient mitochondria in heart muscle cells maintain ATP production so that the heart remains functional as a vital organ.

There are further beneficial effects to the cardiovascular system resulting from the consumption of magnesium bicarbonate. First, decreased fatty acid synthesis in body cells results in lowered body weight with subsequent reduction in high blood pressure to a normal value. Indeed, these effects were observed in people participating in the trial. reported in Example 5. Second, lysosomal enzyme damage to ischaemic heart muscle may be prevented or decreased.

There is unequivocal evidence of correlation that heart disease, senescence, degenerative diseases and death are caused by inefficient mitochondria. Though inefficient mitochondria may not be the only cause of these conditions. There is sufficient evidence however that senescence and general degeneration in all species studied, from fungi to humans, are correlated to the damage to the complex molecules of the mitochondria. For example, the mitochondria of aged people carry nucleic acid and protein defects not observed in the mitochondria of young people. This is true particularly of the mitochondria in muscle, heart and brain cells. Accordingly, it has been proposed that several chronic diseases common in old age may be related to mitochondrial failure, including heart disease, late-onset diabetes and Parkinson's and Alzheimer's diseases. That is, the gradual loss of efficiency of cell mitochondria results in a diminution of the functional capacity of body cells with pathological consequences.

A progressive decline in organ function is characteristic of old age. Some of the changes that occur as people grow older are:
1. The ability to focus the eyes decreases and response time to stimuli becomes slower.
2. Cancers in epithelial tissues (skin, lung, colon, mammary gland) become more common.
3. Heart disease and widely disseminated atherosclerosis occur.
4. Osteoporosis and bone and joint pathology occur.
5. Thermoregulation becomes impaired.
6. There is a decline in the ability of body organs such as the reproductive organs, lungs, glandular tissues and kidneys to maintain their specialised life processes.
7. There is a reduced capacity for surviving haemorrhage.
8. There is an increase in autoinimrnune diseases and chronic inflammatory diseases.

Relative to their life span of around three years, mice develop heart disease, kidney disease, arthritis and cancer at similar stages in life to humans. In other words, both senescence and the similar degenerative diseases of mice and humans are correlated to the chronological age of each species but cannot be linked causally to chronological age per se. It has been observed in many experiments that rodents fed caloric restricted diets suffer less from the above diseases than control animals. It has been observed also that careful necropsies on diet-restricted rodents often do not reveal any gross or microscopic pathology.

Mitochondrial proton leak is a contributing cause of mitochondrial inefficiency and hence a source of senescence and degenerative diseases in short-lived rodents. Mitochondrial proton leak may be a source of senescence and degenerative diseases in humans. Because the proton leak in humans is only a fraction of the leak in rodents, humans develop senescence and degenerative diseases at a later chronological age than rodents.

It may be possible to prevent inefficient processes in mitochondria in order to extend longevity and to delay degenerative diseases. Exogenous sources of appropriate bicarbonate anions can be absorbed by body cells to maintain intracellular alkaline pH values and that alkaline pH values maintain mitochondrial respiration rates and maintain effective proton concentration gradients across inner mitochondrial membranes.

Intracellular alkaline pH values appear necessary for optimum activities of many enzymes in body cells. These enzymes include polymerases, phosphofructokinase and carbonic anhydrase. Enzymes permit life processes to be perpetuated. Therefore, maintenance of enzyme activities by maintenance of intracellular alkaline pH values may assist in the perpetuation of longevity.

The long-term provision of appropriate bicarbonate anions to body cells maintains efficient mitochondrial function, maintains the DNA polymerase activity of mitochondria and therefore maintains the integrity of mitochondrial DNA. This latter effect results in accurate syntheses of the complex functional molecules that are involved in electron fluxes in mitochondria. Of course, bicarbonate anions will decrease the proton load per se in body cells with a subsequent decrease in proton damage to other cell molecules and a decrease in the tendency of oxidation reactions to occur. Decreased oxidations result in decreased DNA mutations and decreased amino acid oxidations. Degenerative diseases are delayed.

INDUSTRIAL APPLICABILITY

An aqueous metal bicarbonate solution of the invention can be readily utilised in medicine to prevent and to treat certain inflammatory diseases, degenerative diseases and viral diseases in mammals.

What is claimed is:
1. An aqueous alkali metal bicarbonate solution for oral administration wherein the alkali metal is substantially only magnesium ions, comprising a stabilising agent selected from the group consisting of carbon dioxide, hydrated carbon dioxide, carbonic acid and any mixture thereof, the stabilising agent being present in an amount whereby the pH of the solution is maintained above the normal blood plasma H value of 7.38 and below about 9.

2. The aqueous alkali metal bicarbonate solution of claim 1, wherein the bicarbonate anions are present in a concentration of from 150 mg per liter to 3500 mg per liter of the solution.

3. The aqueous alkali metal bicarbonate solution of claim 1, wherein the metal cations are present in a concentration of from 30 mg per liter to 140 mg per liter of the solution.

4. The aqueous alkali metal bicarbonate solution according to claim 1, wherein the pH of the said solution is maintained at a value selected from the group consisting of pH 7.5 to 8.8, pH 7.5 to 8.5, pH 7.8 to 8.6, pH 7.8 to 8.5, pH 7.8 to 8.4, pH 7.8 to 8.3, pH 7.8 to 8.2, pH 7.8 to 8.1, pH 7.8 to 8.0, pH 7.8 to 7.9, pH 7.9 to 8.6, pH 7.9 to 8.5, pH 7.9 to 8.4, pH 7.9 to 8.3, pH 7.9 to 8.2, pH 7.9 to 8.1, pH 7.9 to 8.0, pH 8.0 to 8.6, pH 8.0 to 8.5, pH 8.0 to 8.4, pH 8.0 to 8.3, pH 8.0 to 8.2, pH 8.0 to 8.1, pH 8.1 to 8.6, pH 8.1 to 8.5, pH 8.1 to 8.4, pH 8.1 to 8.3, pH 8.1 to 8.2, pH 8.2 to 8.6, pH 8.2 to 8.5, pH 8.2 to 8.4, pH 8.2 to 8.3, pH 8.3 to 8.6, pH 8.3 to 8.5, pH 8.3 to 8.4, pH 8.4 to 8.6, pH 8.4 to 8.5, pH 8.5 to 8.6, pH 8 to 8.5, pH 8.2 to 8.6 and pH 8.3.

5. An aqueous alkali metal bicarbonate solution for preventing or treating inflammatory diseases, degenerative diseases or viral diseases in a mammal, wherein the alkali metal is substantially only magnesium ions, comprising a stabilising agent selected from the group consisting of carbon dioxide, hydrated carbon dioxide, carbonic acid and any mixture thereof, the stabilising agent being present in an amount whereby the pH of the solution is maintained above a normal blood plasma pH value of 7.38 and below about 9, the concentration of the said magnesium ions in the solution being therapeutically effective to prevent or to treat the said disease.

6. An aqueous magnesium bicarbonate solution for decreasing or treating senescence or increasing longevity in a mammal, wherein the alkali metal is substantially only magnesium ions, comprising a stabilising agent selected from the group consisting of carbon dioxide, hydrated carbon dioxide, carbonic acid and any mixture thereof, the stabilising agent being present in an amount whereby the pH of the solution is maintained above a normal blood plasma pH value of 7.38 and below about 9, the concentration of the said magnesium ions in the solution being therapeutically effective to decrease or to treat senescence or to increase longevity.

7. A solution for scavenging protons in a mammal, comprising the aqueous alkali metal bicarbonate solution of claim 1 wherein the magnesium bicarbonate is present in the solution in an amount effective to scavenge protons.

8. A solution for decreasing proton concentrations in a mammal, comprising the aqueous alkali metal bicarbonate solution of claim 1, wherein the metal bicarbonate is present in the solution in an amount effective to decrease proton concentrations in the mammal.

9. A solution for decreasing inflammation and inflammatory conditions in a mammal, comprising the aqueous alkali metal bicarbonate solution of claim 1, wherein the metal bicarbonate is present in the solution in an amount effective to decrease inflammation and inflammatory conditions in the mammal.

10. An aqueous alkali metal bicarbonate solution for increasing motor activity or decrease fatigue in a mammal, wherein the alkali metal is substantially only magnesium ions, comprising a stabilising agent selected from the group consisting of carbon dioxide, hydrated carbon dioxide, carbonic acid and any mixture thereof, the stabilising agent being present in an amount whereby the pH of the solution is maintained above a normal blood plasma pH value of 7.38 and below about 9, the concentration of the said magnesium ions in the solution being therapeutically effective to increase motor activity or decrease fatigue.

11. A method of scavenging protons in a mammal, comprising administering to the mammal the aqueous alkali metal bicarbonate solution of claim 1, wherein the magnesium bicarbonate is present in the solution in an amount effective to scavenge protons in said mammal.

12. A method of decreasing proton concentrations in a mammal by altering carbonic anhydrase enzyme reactions in said mammal comprising administering to said mammal an effective amount of the aqueous alkali metal bicarbonate solution of claim 1.

13. The method of any one of claims 11 or 12 wherein said mammal is human and said aqueous alkali metal carbonate solution is administered to said human on an empty stomach.

14. A substantially clear aqueous alkali metal bicarbonate solution as claimed in claim 1, comprising a pH adjusting agent in the solution in an amount whereby the pH of the solution is adjusted to exceed the normal blood plasma pH value of 7.38 and to be below about 9, and a stabilising agent in an amount effective to ensure that the solution remains substantially clear.

15. A process of preparing an aqueous alkali metal carbonate solution, wherein the alkali metal is substantially only magnesium ions, the solution comprising a stabilising agent selected from the group consisting of carbon dioxide, hydrated carbon dioxide, carbonic acid and any mixture thereof, the stabilising agent being present in an amount whereby the pH of the solution is maintained above a normal blood plasma pH value of 7.38 and below about 9, the process comprising reacting magnesium carbonate powder with an effective amount of carbon dioxide to solubilize the magnesium carbonate and produce the said solution.

16. An aqueous magnesium bicarbonate solution, whenever prepared by the process of claim 15.

17. An aqueous alkali metal bicarbonate solution for preventing or treating arthritis in a mammal, wherein the alkali metal is substantially only magnesium ions, the solution comprising a stabilising agent selected from the group consisting of carbon dioxide, hydrated carbon dioxide, carbonic acid and any mixture thereof, the stabilising agent being present in an amount whereby the pH of the solution is maintained above a normal blood plasma pH value of 7.38 and below about 9, the concentration of the said magnesium ions in the solution being therapeutically effective to prevent or treat arthritis.

18. An aqueous alkali metal bicarbonate solution for oral administration as claimed in claim 1, wherein the pH of the solution is from about 8.2 to about 8.8.

19. An aqueous alkali metal bicarbonate solution for oral administration as claimed in claim 18, which is substantially clear.

20. An aqueous alkali metal bicarbonate solution for oral administration as claimed in claim 19, wherein the stabilising agent is selected such as to substantially prevent the precipitation of magnesium carbonate from the solution.

21. An aqueous alkali metal bicarbonate solution for oral administration as claimed in claim 20, packaged, ready for use, in a sealed container.

* * * * *

UNITED STATES PATENT AND TRADEMARK OFFICE
CERTIFICATE OF CORRECTION

PATENT NO.     : 6,544,561 B2
DATED          : April 8, 2003
INVENTOR(S)    : Russell John Beckett It is certified that error appears in the above-identified patent and that said Letters Patent is hereby corrected as shown below:

Column 48,
Line 48, replace "H value of 7.38 and below about 9" with
-- pH value of 7.38 and below about 9 --.

Signed and Sealed this

Sixteenth Day of September, 2003

JAMES E. ROGAN
*Director of the United States Patent and Trademark Office*